(12) United States Patent
Port et al.

(10) Patent No.: US 8,367,039 B2
(45) Date of Patent: Feb. 5, 2013

(54) COMPOUNDS FOR THE DIAGNOSIS OF DISEASES ASSOCIATED WITH VCAM EXPRESSION

(75) Inventors: Marc Port, Deuil la Barre (FR); Olivier Rousseaux, Senlis (FR); Robert Muller, Mons (BE); Carmen Burtea, Mons (BE)

(73) Assignee: Guerbet, Villepinte (FR)

( * ) Notice: Subject to any disclaimer, the term of this patent is extended or adjusted under 35 U.S.C. 154(b) by 428 days.

(21) Appl. No.: 12/593,175

(22) PCT Filed: Mar. 28, 2008

(86) PCT No.: PCT/EP2008/053768
§ 371 (c)(1),
(2), (4) Date: Mar. 26, 2010

(87) PCT Pub. No.: WO2008/125464
PCT Pub. Date: Oct. 23, 2008

(65) Prior Publication Data
US 2011/0200533 A1    Aug. 18, 2011

(30) Foreign Application Priority Data
Mar. 28, 2007   (FR) ...................................... 07 54087

(51) Int. Cl.
*A61K 49/00*   (2006.01)
(52) U.S. Cl. ....... 424/9.1; 424/1.11; 424/1.65; 424/1.69
(58) Field of Classification Search ................ 424/1.11, 424/1.65, 1.69, 1.81, 1.85, 1.89, 9.1, 9.2, 424/9.3, 9.4, 9.5, 9.6, 9.7, 9.8; 514/1, 1.11; 530/300, 328; 534/7, 10–16
See application file for complete search history.

(56) References Cited

U.S. PATENT DOCUMENTS

| | | | |
|---|---|---|---|
| 5,080,885 A | 1/1992 | Long, Jr. | |
| 5,919,432 A | 7/1999 | Meyer et al. | |
| 5,958,371 A | 9/1999 | Lanza et al. | |
| 5,989,520 A | 11/1999 | Lanza et al. | |
| 6,010,682 A | 1/2000 | Unger et al. | |
| 6,045,821 A | 4/2000 | Garrity et al. | |
| 6,110,457 A | 8/2000 | Belshe et al. | |
| 6,264,914 B1 | 7/2001 | Klaveness et al. | |
| 6,403,056 B1 | 6/2002 | Unger | |
| 6,440,956 B1 | 8/2002 | Port | |
| 6,537,520 B1 | 3/2003 | Rajopadhye et al. | |
| 6,676,963 B1 | 1/2004 | Lanza et al. | |
| 2002/0048763 A1 | 4/2002 | Penn et al. | |
| 2002/0090342 A1 | 7/2002 | Liu | |
| 2002/0098149 A1 | 7/2002 | Liu | |
| 2003/0077288 A1 | 4/2003 | Goldberg et al. | |
| 2004/0248856 A1 | 12/2004 | Lanza et al. | |
| 2004/0253181 A1 | 12/2004 | Port et al. | |
| 2005/0100963 A1 | 5/2005 | Sato et al. | |
| 2006/0018830 A1 | 1/2006 | Cappelletti et al. | |
| 2006/0239913 A1 | 10/2006 | Port et al. | |
| 2009/0021441 A1 | 1/2009 | Ohno | |
| 2009/0208408 A1 | 8/2009 | Boturyn et al. | |

FOREIGN PATENT DOCUMENTS

| | | |
|---|---|---|
| DE | 10 2004 062 258 B3 | 1/2006 |
| EP | 0 661 279 B1 | 3/2001 |
| FR | 2 876 033 A1 | 4/2006 |
| WO | WO 90/04943 A1 | 5/1990 |
| WO | WO 01/60416 A2 | 8/2001 |
| WO | WO 02/26776 A2 | 4/2002 |
| WO | WO 02/055111 A2 | 7/2002 |
| WO | WO 02/085908 A1 | 10/2002 |
| WO | WO 03/011115 A2 | 2/2003 |
| WO | WO 03/038130 A2 | 5/2003 |
| WO | WO 03/062198 A1 | 7/2003 |
| WO | WO 2004/058275 A2 | 7/2004 |
| WO | WO 2004/112840 A2 | 12/2004 |
| WO | WO 2006/031885A2 A2 | 3/2006 |
| WO | WO 2006/032705 A2 | 3/2006 |
| WO | WO 2006/069676 A1 | 7/2006 |
| WO | WO 2006/100305 A2 | 9/2006 |

OTHER PUBLICATIONS

Kelly, Kimberly et al. "Detection of Vascular Adhesion Molecule-1 Expression Using a Novel Multimodal Nanoparticle" (Ciro. Res. 2005, vol. 96, pp. 327-336).

*Primary Examiner* — D L Jones
(74) *Attorney, Agent, or Firm* — Birch, Stewart, Kolasch & Birch, LLP

(57) ABSTRACT

The present invention relates to a compound of the following general formula (I): Signal-Linker-Peptide (I) in which Signal is a signal entity; Linker, is absent or is a chemical bond, and Peptide is a peptide having a VCAM-targeting peptide and pharmaceutically acceptable salts thereof. The VCAM-targeting peptide may be X10-X11-X12-X13-X14-X15-X16-X17-X18 (SEQ ID No. 4) with X10 chosen from cysteine and methionine; X11 chosen from methionine and cysteine; X12 chosen from lysine, arginine and alanine; X13 chosen from threonine and serine; X14 chosen from aspartic acid and glutamic acid; X15 chosen from threonine and serine; X16 chosen from arginine, alanine and lysine; X17 chosen from leucine, isoleucine and valine; X18 chosen from cysteine and methionine; preferably, the peptide CMKT-DTRLC (SEQ ID No. 5).

13 Claims, 3 Drawing Sheets

COMPOUNDS FOR THE DIAGNOSIS OF DISEASES ASSOCIATED WITH VCAM EXPRESSION

Figure 1:
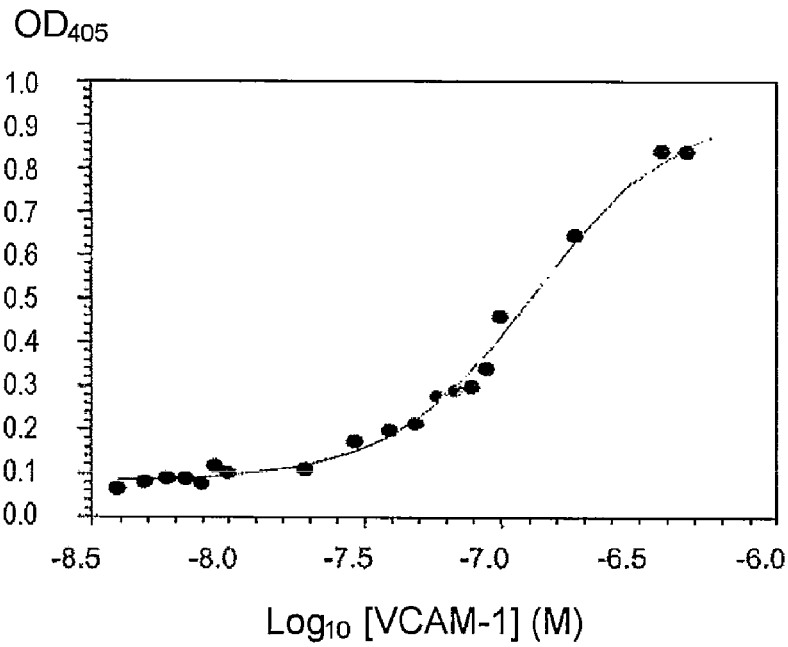

The invention relates to novel compounds for diagnosing diseases related to VCAM expression, to the method for the preparation thereof and to the use thereof in medical imaging.

VCAM-1 (vascular cell adhesion molecule-1) is an immunoglobulin of interest, in particular diagnostic interest, in cardiovascular pathological conditions. This is because VCAM-1 is a marker for regions predisposed to becoming atheromatous. VCAM-1 is highly overexpressed on activated endothelial cells. Like other adhesion molecules, such as ICAM-1, 2 and 3, VCAM-1 is involved in the adhesion of leukocytes to the endothelium during atherosclerosis. Several in vivo models have been described. In advanced atherosclerotic regions, VCAM-1 expression is positive on the endothelium capping the plaque; VCAM-1 is also present on the endothelial cells in proximity to the lesions and it is very abundant in the intima, at the smooth muscle cell level.

In humans, VCAM-1 expression in human atherosclerotic aortic and femoral arteries has been described in the following way:
artery with a normal appearance: weak expression at the level of the endothelium;
artery with thickening of the neointima, without macrophage infiltration: slight endothelial increase in VCAM-1;
developed lesion, containing "mature" macrophages: expression doubled in comparison with the previous situation;
developed lesion, comprising recent macrophage infiltration: immunolabeling significantly higher, covering a greater part of the endothelial region.

At the level of the coronary arteries, VCAM-1 is expressed only on the endothelium of the plaques, and not at the level of the healthy walls.

In the oncology field, VCAM participates in the adhesion of lymphocytes, of monocytes and of eosinophils to endothelial cells activated via alpha4beta1 integrin. It is strongly expressed in pathological conditions such as chronic ulcerative colitis or Crohn's disease. Like ICAM-1, it is thought to be overexpressed at the periphery of cancers and might participate in metastatic processes.

Attempts are continually being made to improve the quality of the in vivo diagnosis of cardiovascular and cancerous diseases by means of novel, very specific markers, intended for imaging methods known to those skilled in the art, in particular MRI, X-rays, gamma-ray scintigraphy, CT scan, ultrasound, PET and optical imaging. It is recalled that, in the case of MRI, a contrast is obtained through the administration of contrast agents containing paramagnetic or superparamagnetic metals which have an effect on the relaxivity of the protons of water. In the case of scintigraphy, the contrast is obtained by the specific localization of a radiopharmaceutical compound which emits gamma- or beta-rays.

Compounds for which the chemical synthesis is not too complex, which are sufficiently stable in vivo for use in medical imaging and the cost price of which is not too high are sought, in particular for MRI so as not to use radioactive elements, the use of which is complex.

The applicant has succeeded in obtaining compounds comprising a VCAM-region-targeting portion, which are effective not only in vitro but also and especially in MRI in vivo. Such compounds are in fact difficult to obtain since it is necessary not only to identify a biovector which is effective in vitro, but also to obtain a compound which is effective in human clinical diagnostic imaging. This is particularly the case for MRI, which is recognized as being a highly sought-after technique since it does not use radioactivity, but the sensitivity of which is very much lower than that of nuclear medicine.

The compound obtained should at the same time have sufficient affinity to recognize its target, a high specificity so as to be a distinctive indicator of the pathological state and an appropriate stability so as not to be degraded or modified in vivo; and, in addition, without the signal portion interfering so as to impair these various parameters (affinity and stability in particular).

After many attempts, the applicant has succeeded in obtaining effective compounds.

The invention thus relates to a compound of general formula (I) below:

Signal-Linker-Peptide    (I)

in which:
Signal represents a signal entity;
Linker, which may or may not be present, represents a chemical bond, and
Peptide represents a peptide comprising a VCAM-targeting peptide, the VCAM-targeting peptide being chosen from the peptides of formula below and the functional equivalents thereof:

a) X1-X2-X3-X4-X5-X6-X7-X8-X9 (1) (SEQ ID No. 1)
where:
X1 is absent or chosen from cysteine and methionine
X2 chosen from asparagine and glutamine
X3 chosen from asparagine and glutamine
X4 chosen from serine and threonine
X5 chosen from lysine, arginine, histidine and ornithine
X6 chosen from serine and threonine
X7 chosen from histidine, arginine and lysine
X8 chosen from threonine and serine
X9 is absent or chosen from cysteine and methionine
preferably, the peptide CNNSKSHTC (SEQ ID No. 2) (Cys-Asn-Asn-Ser-Lys-Ser-His-Thr-Cys) and the peptide NNSKSHT (SEQ ID No. 3);

b) X10-X11-X12-X13-X14-X15-X16-X17-X18 (2) (SEQ ID No. 4) with:
X10 chosen from cysteine and methionine
X11 chosen from methionine and cysteine
X12 chosen from lysine, arginine and alanine
X13 chosen from threonine and serine
X14 chosen from aspartic acid and glutamic acid
X15 chosen from threonine and serine
X16 chosen from arginine, alanine and lysine
X17 chosen from leucine, isoleucine and valine
X18 chosen from cysteine and methionine
preferably, the peptide CMKTDTRLC (SEQ ID No. 5) (Cys-Met-Lys-Thr-Asp-Thr-Arg-Leu-Cys);
and the pharmaceutically acceptable salts of these compounds of a) or of b).

The expression "VCAM-targeting peptide" is also denoted VCAM PEPTIDE in the application. Advantageously, Peptide represents a VCAM PEPTIDE.

Advantageously, the VCAM PEPTIDE according to the invention comprises at most 20 amino acids, advantageously at most 15 amino acids, advantageously at most 10 amino acids.

Advantageously, the KIAA0137 protein and the HPIV-3 protein are excluded from the VCAM PEPTIDES according to the invention, in particular when Signal represents a label for optical imaging, such as a fluorescent molecule. The KIAA0137 protein is in particular described in patent application WO 03/038130 and the HPIV-3 protein is in particular described in U.S. Pat. No. 6,110,457.

The expression "Peptide CNNSKSHTC (SEQ ID No. 2), NNSKSHT (SEQ ID No. 3) and the functional equivalents thereof" is intended to mean the peptide CNNSKSHTC (SEQ ID No. 2), the peptide NNSKSHT (SEQ ID No. 3), the effectiveness of which has been demonstrated by the applicant, the derived peptides of formula X1-X2-X3-X4-X5-X6-X7-X8-X9 (1) (SEQ ID No. 1) which, once included in the compound (I), exhibit an effectiveness in imaging that is similar to or better than CNNSKSHTC (SEQ ID No. 2) (which includes the peptidomimetics), this effectiveness being tested by means of in vivo tests and models described in detail in the application or of suitable analogous models. The peptide CNNSKSHTC (SEQ ID No. 2) studied is a cyclic peptide and is exemplified in detail in the application.

Similarly, the expression "CMKTDTRLC (SEQ ID No. 5) and the functional equivalents thereof" is intended to mean the peptide CMKTDTRLC (SEQ ID No. 5), the effectiveness of which has been demonstrated by the applicant, and the effective derived peptides of formula X10-X11-X12-X13-X14-X15-X16-X17-X18 (2) (SEQ ID No. 4) The peptide CMKTDTRLC (SEQ ID No. 5) studied is a cyclic peptide and is exemplified in detail in the application.

In particular a derivative of the peptide CNNSKSHTC (SEQ ID No. 2) and NNSKSHT (SEQ ID No. 3) includes a peptide or compound in which the NNSKSHT (SEQ ID No. 3) constituting the sequence has been modified by the addition, deletion, substitution or modification of at least one amino acid.

The substitution may be conservative or nonconservative. The substitution is conservative when an amino acid is substituted with an amino acid having similar properties (for example, polarity, hydrogen-bonding potential, acidity, basicity, hydrophobicity, presence of an aromatic group, etc.). A natural amino acid can be replaced with an unnatural amino acid, such as an amino acid in D configuration, a beta-amino acid or a gamma-amino acid. The VCAM PEPTIDE is, for example, modified using suitable methodologies described in the prior art, for example in US2005100963 (column 20-21, paragraphs [529] to [541] in the case of peptides targeting KDR receptors), in order to select effective compounds (I).

In the case of CNNSKSHTC (SEQ ID No. 2) and NNSKSHT (SEQ ID No. 3),
- N, asparagine, can be replaced with another amino acid carrying an amide chain, in particular glutamine, or substituted derivatives, for example alkyl-substituted derivatives;
- S, serine, can be replaced with another amino acid carrying a hydroxyl group, for example threonine or homoserine;
- K, lysine, can be replaced with other dibasic amino acids (arginine, histidine, ornithine) or derivatives of lysine or of these other amino acids, for example substituted with C1 to C10 alkyls;
- H, histidine, can be replaced with other basic hydrophilic amino acids, in particular arginine or lysine;
- T, threonine, can be replaced with serine.

The NNSKSHT sequence (SEQ ID No. 3) can be modified by replacing one or more amide bonds with a bond which confers increased stability in vivo, for example which confers increased resistance to proteolysis.

The expression "peptide comprising at least one VCAM-targeting peptide" is intended to mean a peptide which exhibits this peptide sequence for recognition of the biological target, optionally flanked, at the N- and/or C-terminal end, by a chemical group that does not interfere with the effectiveness of this sequence in imaging.

The term "Signal" or "signal entity" is intended to mean a chemical entity which makes it possible to obtain a signal in medical imaging, in particular:
- a chelate capable of being coupled to a paramagnetic metal,
- a metal nanoparticle, in particular a superparamagnetic nanoparticle of iron oxide,
- a lipid nanoparticle, advantageously in the form of an emulsion, this nanoparticle carrying at least one chelate capable of being coupled to a paramagnetic metal (in this case, the Peptide is grafted to the lipid nanoparticle in emulsion, which itself carries chelates; the bonding of the peptide to the lipid nanoparticle is, for example, carried out by means of a chemical linking group).

According to one embodiment, the signal entity comprises at least one chelate Ch (in a form complexing a metal M). Advantageously, the chelate is coupled to the metal M. Advantageously, the metal M is a paramagnetic-metal ion, or a radionucleide. The complex formed by the chelate and the metal M is stable under physiological conditions so as to avoid undesired release of the metal M in the body. Advantageously, the chelate or the signal entity comprises at least one functional group for linking the signal entity to the Linker or directly to the Peptide. The invention also relates to the compounds of formula (I) in which the chelate is not complexed with the metal.

Advantageously, Ch is a linear chelate chosen from: EDTA, DTPA diethylenetriaminopentaacetic acid, N-[2-[bis(carboxymethyl)amino]-3-(4-ethoxyphenyl)propyl]-N-[2-[bis(carboxymethyl)amino]ethyl]-L-glycine (EOB-DTPA), monoamide or bisamide derivatives of DTPA, such as N,N-bis[2-[carboxymethyl[(methylcarbamoyl)-methyl]amino] ethyl]glycine (DTPA-BMA), or 4-carboxy-5,8,11-tris(carboxymethyl)-1-phenyl-2-oxa-5,8,11-triazatridecan-13-oic acid (BOPTA).

Advantageously, Ch is a macrocyclic chelate chosen from 1,4,7,10-tetraazacyclododecane-1,4,7,10-tetraacetic acid (DOTA), 1,4,7,10-tetraazacyclododecane-1,4,7-triacetic acid (DO3A), 10-)2-hydroxypropyl)-1,4,7,10-tetraazacyclododecane-1,4,7-triacetic acid (HPDO3A), 2-methyl-1,4,7,10-tetraazacyclododecane-1,4,7,10-tetraacetic acid (MCTA), (alpha, alpha', alpha'', alpha''')-tetramethyl-1,4,7,10-tetraazacyclododecane-1,4,7,10-tetraacetic acid (DOTMA), 3,6,9,15-tetraazabicyclo[9.3.1]pentadeca-1(15), 11,13-triene-3,6,9-triacetic acid (PCTA), 1,4,7-triazacyclononane-N,N',N44-triacetic acid (NOTA), AAZTA (described in particular in WO 2006/00273, formula III, page 120 and US 2006/00118830, pages 2 and 89), TETA, TETMA, PDTA, and their benzo derivatives, LICAM, MECAM and HOPO (DE 102004062258).

Ch may also be a derivative of these compounds, in which one or more carboxylic groups is (are) in the form of a corresponding salt, ester or amide; or a corresponding compound in which one or more carboxylic groups is (are) replaced with a phosphonic and/or phosphinic group.

Use may also be made of a chelate chosen from: DOTA gadofluorines, DO3A, HPDO3A, TETA, TRITA, HETA, DOTA-NHS, M4DOTA, M4DO3A, PCTA and their derivatives, advantageously chosen from: DOTA, DTPA, DO3A, HPDO3A, TRITA, TETA, BOPTA, NOTA, PCTA, DOTMA, AAZTA, HOPO and their derivatives.

More broadly, the chelate(s) forming the signal entity may correspond to the following formula of document WO 01/60416:

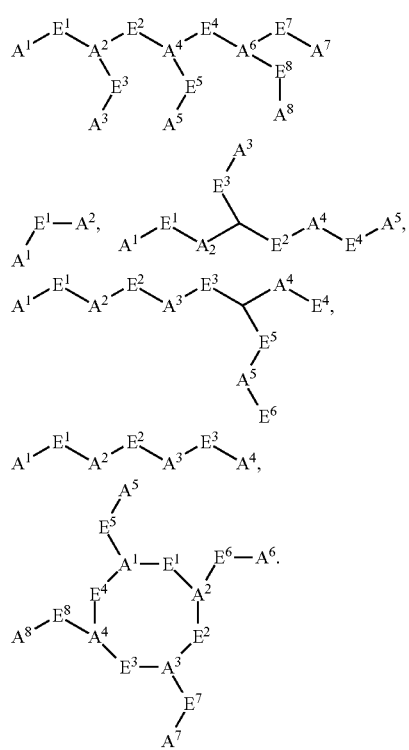
Use may in particular be made of the compounds DTPA, DOTA, NOTA, DO3A, and derivatives. Mention will also be made of the chelates recalled in WO 03/011115, in particular having the formulae below:
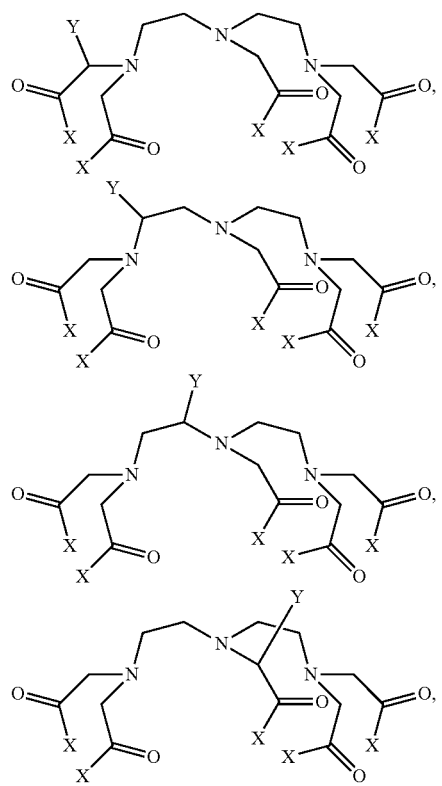
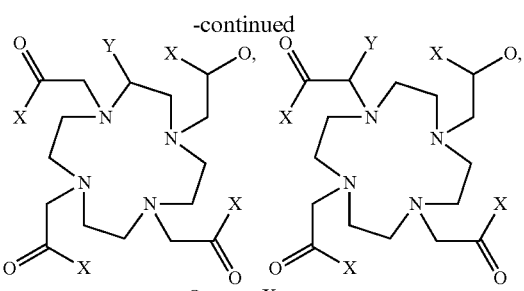
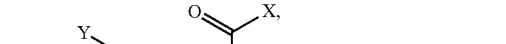
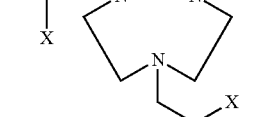
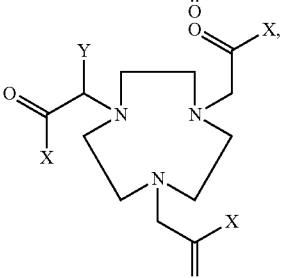
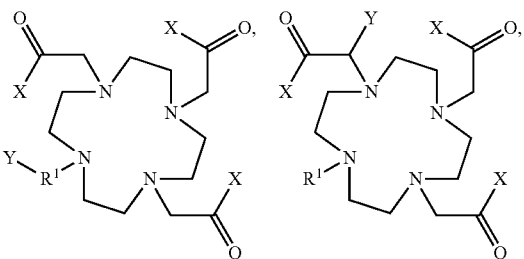
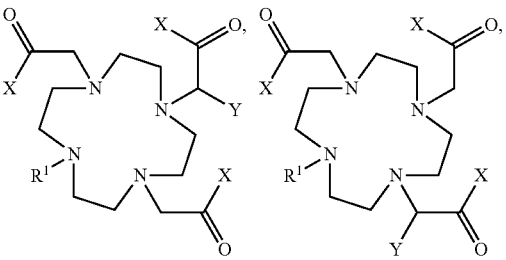
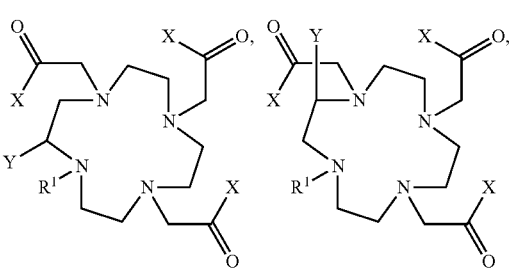

-continued

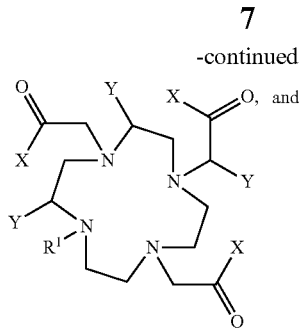

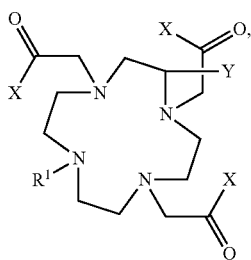

with X being a group capable of coordinating a metal cation, preferably O—, OH, NH$_2$, OPO$_3$— or NHR with R being an aliphatic chain, and Y a chemical linker.

Use may in particular be made of the chelates denoted P730, of the applicant, described in EP 661 279 (U.S. Pat. No. 5,919,432), having the formula:

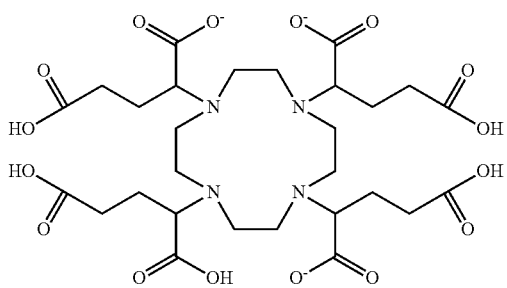 [SMILES: O=C(O)CCC(C(=O)[O-])N1CCN(C(CCC(=O)O)C(=O)[O-])CCN(C(CCC(=O)O)C(=O)O)CCN(C(CCC(=O)O)C(=O)[O-])CC1]

and the chelates with a PCTA backbone, described by the applicant in particular in U.S. Pat. No. 6,440,956, whether or not these chelates or their intermediates carry hydrophilic chains, and in particular short or long amino alcohol chains.

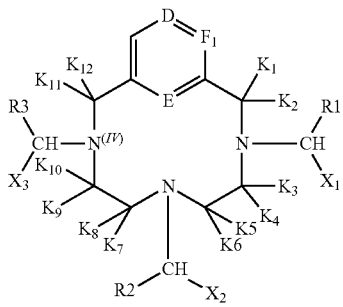

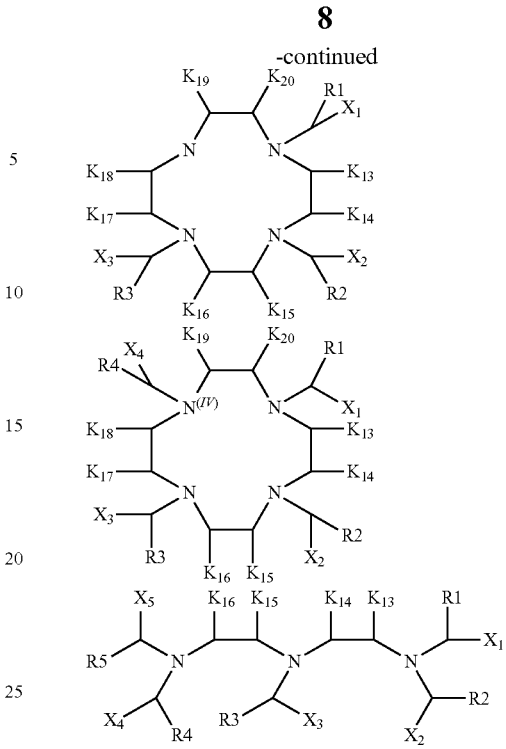

with X1 to X4 and K1 to K16 of the above chelates representing H or a $C_1$-$C_{20}$ chain, and R1, R2, R3, R4, R5 independently representing —COOH or —P(O)(OH)$_2$; and being chosen such that the chelate comprises at least one function capable of being coupled to a VCAM PEPTIDE directly or by means of the Linker.

Mention will also be made of the chelates of document US2006/0018830, pages 9 to 11 of the description section [0150] to [0158].

Advantageously, in the context of the present invention, Ch is DTPA or DOTA or their derivatives.

In the case of MRI, the relaxivity $r_1$ of these chelates is typically of the order of 4 to 20 s$^{-1}$ mMol$^{-1}$ Gd$^{-1}$ with a field of 0.5 to 1.5 T. It is recalled that the longitudinal relaxivity $r_1$ of a paramagnetic contrast product gives the measure of its magnetic effectiveness and makes it possible to assess its influence on the recorded signal.

In MRI medical imaging, the contrast products modify the proton relaxation time, and the increase in relaxivity obtained makes it possible to obtain a higher signal.

In formula I, the term "chemical bond" is intended to mean a linking group or Linker L, i.e. a chemical group:
- which makes it possible to link the Signal and the VCAM PEPTIDE(s),
- which does not itself have the signal entity function that is provided by the Signal,
- which does not itself have the targeting function that is provided by the VCAM PEPTIDE.

The coupling of chelates with biovectors, in particular peptides, is described in the prior art, and generally involves a chemical bond (Linker) as described in document WO 01/60416. The structure and the chemical nature of the chemical bond are defined so as to enable chemical coupling between the peptide portion of the VCAM PEPTIDE and the chelate(s) used, and in such a way as to obtain an affinity of the VCAM PEPTIDE portion for its target and a specificity of recognition suitable for the use.

A large number of Linkers can be used, in so far as they are capable of interacting with at least one biovector functional group and at least one chelate functional group.

Advantageously, Linker represents:

a) a group of formula Q1-1-Q2,
in which Q1 and Q2, which may be identical or different, represent O, S, NH, CO$_2$, —NHCO, CONH, NHCONH, NHCSNH, SO$_2$NH— or NHSO$_2$—,
and 1 represents an alkyl group (advantageously C$_1$-C$_{10}$), alkoxyalkyl group (advantageously C$_1$-C$_{10}$), alkenyl group (advantageously C$_2$-C$_6$), alkynyl group (advantageously C$_2$-C$_6$), polyalkoxyalkylene group, alkyl group interrupted with one or more squarates, with one or more aryls, advantageously phenyl, or with one or more groups chosen from —NH—, —O—, —CO—, —NH(CO)—, —(CO)NH—, —O(CO)— or —(OC)O—;

b) a (CH$_2$)$_n$, (CH$_2$)$_n$—CO—, —(CH$_2$)$_n$NH—CO—, where n=1 to 10, (CH$_2$CH$_2$O)$_q$ (CH$_2$)$_r$—CO—, (CH$_2$CH$_2$O)$_q$ (CH$_2$)$_r$—NH—CO—, where q=1-10 and r=1-10, (CH$_2$)$_n$—CONH—, (CH$_2$)$_n$—CONH-PEG, (CH$_2$)$_n$—NH—,

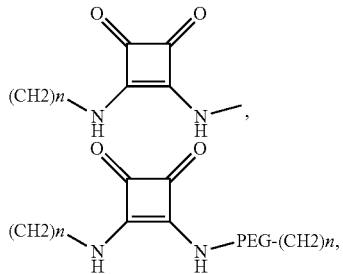

(CH$_2$)$_n$-squarate-(CH$_2$CH$_2$O)$_q$(CH$_2$)$_r$CO where n=1 to 5 and advantageously n=3, 4 or 5, HOOC—CH$_2$—O—(CH$_2$)$_2$—O—(CH$_2$)$_2$—O—CH$_2$—COOH; HOOC—(CH$_2$)$_2$—CO$_2$—(CH$_2$)$_2$—OCO—(CH$_2$)$_2$—COOH; HOOC—CH(OH)—CH(OH)—COOH; HOOC—(CH$_2$)$_n$—COOH; NH$_2$—(CH$_2$)$_n$—NH$_2$, where n=1-20; NH$_2$—(CH$_2$)$_n$—CO$_2$H; or NH$_2$—CH$_2$—(CH$_2$—O—CH$_2$)$_n$—CO$_2$H, with n=1 to 10, group;

In particular:

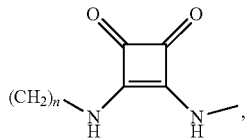

(CH$_2$)$_m$ where n=1 to 4 and m=0 to 5

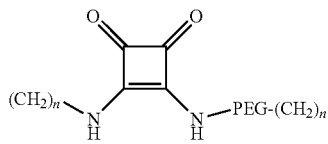

where n=1 to 4 and m=0 to 5
(CH$_2$)$_n$—CO where n=1 to 5
(CH$_2$)$_3$-squarate-(CH$_2$CH$_2$O)$_2$(CH$_2$)—CO;

c) linkers described in U.S. Pat. No. 6,264,914, capable of reacting with amino, hydroxyl, sulfhydryl, carboxyl, carbonyl, carbohydrate, thioether, 2-amino alcohol, 2-aminothiol, guanidinyl, imidazolyl, phenolic functional groups (of the biovector and of the chelate); according to the definitions of this document;

d) certain linkers described in U.S. Pat. No. 6,537,520, of formula:

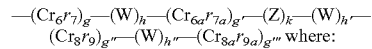
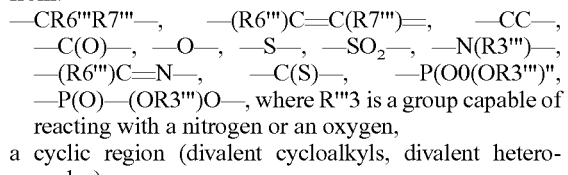

g+h+g'+k+h'+g"+h"+g''' is other than 0; with the definitions identical to those of this document, column 8;

e) certain linkers described in document WO 02/085908 (with the definitions identical to those of this document), for example a linear or branched organic linking chain chosen from:
—CR6'''R7'''—, —(R6''')C═C(R7''')═, —CC—, —C(O)—, —O—, —S—, —SO$_2$—, —N(R3''')—, —(R6''')C═N—, —C(S)—, —P(O0(OR3''')'', —P(O)—(OR3''')O—, where R'''3 is a group capable of reacting with a nitrogen or an oxygen,
a cyclic region (divalent cycloalkyls, divalent heterocycles),
polyalkylenes, polyalkylene glycols;

f) linkers of document WO 03/011115, pages 124-125;

g) linkers of document US 2006/0018830 (the Linker of the applicant corresponding to the linker denoted N—O—P in this document US 2006/0018830),
linkers comprising at least one non-alpha amino acid (pages 12 to 15, table 1 of this document),
linkers comprising at least one non-alpha amino acid carrying a cyclic group (pages 18 to 25, table 3 of this document),
linkers not comprising an amino acid,
other linkers (pages 27, 28 of this document).

The choice of Linker (structure and size) may be carried out in particular in such a way as to control especially the charge, the lipophilicity and/or the hydrophilicity of the product of formula (I), so as to optimize the biological targeting, the biodistribution. Linkers that are biodegradeable in vivo, PEG linkers or mini-PEG linkers may in particular be used.

The linker is chosen in such a way as not to detrimentally alter the effectiveness of the compound of formula (I) according to the invention, a test for verifying this effectiveness in vitro and in vivo being present in the detailed description.

According to another embodiment, Signal represents a label for optical imaging (fluorescent molecule used in optical imaging). Among the labels for optical imaging, mention will in particular be made of those of US2006/0018830, and in particular those cited on pages 11 and 12, paragraph 1.B, with precise imaging modes described in column 33 ([0259]) in paragraph 6 (techniques and chromophores and fluorophores described in detail).

According to another embodiment, Signal represents quantum dots (inorganic fluorophores comprising nanocrystals).

According to another embodiment, Signal represents a superparamagnetic nanoparticle coated with an organic layer, commonly denoted SPIO or USPIO ("ultra small particles of iron oxide"). Advantageously, the nanoparticle comprises a core of iron oxide or hydroxide, in particular of magnetite (Fe$_3$O$_4$), maghemite (γ-Fe$_2$O$_3$). Use will advantageously be made of a nanoparticle covered with a bisphosphonate, advantageously gem-bisphosphonate, coating, described in WO2004058275, the particle and the method for coupling between the peptide and the nanoparticle being described in detail in the examples of the present application. The magnetic nanoparticles used are acidic nanoparticles based on an iron compound, and covered with a layer comprising one or more gem-bisphosphonate compounds, which may be identical or different, the nanoparticle-covering layer having the formula (C) below:

 (C)

in which:
the linker L2 represents an organic group linking the function T to the gem-bisphosphonate —CH(PO$_3$H$_2$)$_2$ function;
T represents a chemical function coupled to the VCAM PEPTIDE or to the Linker of the present application.

In one particular embodiment, T-L2 represents the Linker of the compound of formula (I).

The composition is in the form of a stable aqueous solution of nanoparticles. In these compositions, the degree of complexation of the compound (C) on the particles is greater than 50%, advantageously than 70%, and preferably greater than 80, 90, 95%. It is particularly preferred for the acidic magnetic particles (p) to be complexed on at least 90% of their protonated sites with compounds of formula (C). According to one variant, a part of the functions T of the layer is coupled to a VCAM PEPTIDE, and a part of the functions T is coupled to a hydrophilic compound, in particular a compound carrying hydroxyl groups, and in particular an amino alcohol hydrophilic compound denoted AAG1AA28, described in WO2004058275 (example 8), or a PEG group.

The magnetic particles (p) have a hydrodynamic diameter of between 5 and 300 nm, preferably between 5 and 60 nm, more preferably between 5 and 30 nm.

The linker L2 makes it possible to link and/or to space out the gem-bisphosphonate function and the reactive entity T capable of providing the covalent grafting of the VCAM PEPTIDE (the biovector) onto the nanoparticle, possibly by means of the Linker.

By way of preference, the linker L2 represents a divalent group.

Preferably, the linker L2 is chosen from:
an aliphatic group; alicyclic group; aliphatic alicyclic group; aromatic group; aliphatic aromatic group, it being possible for said aliphatic, alicyclic and aromatic groups to be optionally substituted with a methyl, hydroxyl, methoxy, acetoxy or amido group, or a halogen atom, advantageously a chlorine, iodine or bromine atom;
an -l$_1$—NHCO-l$_2$ group where l$_1$ and l$_2$, which may be identical or different, represent an aliphatic group; alicyclic group; aromatic group; aliphatic alicyclic group or aliphatic aromatic group, it being possible for said groups to be optionally substituted with a methyl, hydroxyl, methoxy, acetoxy or amido group, or a chlorine, iodine or bromine atom.

According to preferred embodiments, L2 represents a substituted or unsubstituted aliphatic group, and more preferably a —(CH$_2$)$_p$— group, where p is an integer from 1 to 5, or preferably a —(CH$_2$)$_n$—NCHO—(CH$_2$)$_m$— group where n and m represent an integer from 0 to 5.

By way of preferred T groups, mention may in particular be made of COOH, —NH$_2$, —NCS, —NH—NH$_2$, —CHO, alkylpyrocarbonyl (–00-O—CO-alk), acylazidyl (—CO—N$_3$), iminocarbonate (—O—C(NH)—NH$_2$), vinylsulfuryl (—S—CH=CH$_2$), pyridyldisulfuryl (—S—S-Py), haloacetyl, maleimidyl, dichlorotriazinyl and halogen groups, particular preference being given to —COOH and —NH$_2$ groups.

Preferably, T represents a —COOH or —NH$_2$ group and L2 a substituted or unsubstituted aliphatic group advantageously a —(CH$_2$)$_p$— group, where p is an integer from 1 to 5.

The layer of formula (C1) below:

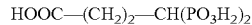

is most particularly preferred.

Several compounds of the type nanoparticles of iron oxide carrying VCAM PEPTIDE are described in the detailed description (in particular, PEG-USPIO).

According to another embodiment, Signal represents a lipid nanoparticle comprising at least one chelate. The lipid nanoparticles may be in the form of a nanoparticulate emulsion, possibly containing perfluorocarbons, such as those described in documents WO 03/062198, U.S. Pat. No. 5,958,371, U.S. Pat. No. 5,080,885 and U.S. Pat. No. 6,403,056.

The lipid nanoparticles may be suspended in an aqueous or hydrophilic medium. These nanoparticles have a diameter of the order of 10 nm to 500 nm, in particular 20 to 250 nm. The nanoparticles in emulsion may comprise or be coupled with a large number of chelates, for example 10 000 to 100 000 chelates per nanoparticle. The emulsions comprise sufficient compounds of formula (I) and therefore of Peptide to allow recognition of the region of apoptosis. As possible nanoparticles, mention will be made of liposomes, which may be unilamellar or multilamellar, micelles, microgels, oil droplets, lipoproteins, such as HDL, LDL, IDL or VLDL, chylomicrons, fluorocarbon nanoparticles, nanobubbles, or the like, the surface of which is lipophilic.

Advantageously, the chelate is lipophilic and attached to the membrane of the nanoparticle.

Advantageously, the Linker of the compound of formula (I) is sufficiently lipophilic for coupling the Peptide to the membrane of the lipid nanoparticle, the VCAM PEPTIDE being sufficiently expressed on the outer part of the nanoparticle for specific recognition of the apoptotic target. The Linker is, for example, a lipophilic group such as a C$_{10}$-C$_{20}$ alkylene chain, this chain being inserted into the lipid layer of the nanoparticle and thus making it possible to attach the Peptide to the nanoparticle.

Many chelates made lipophilic so as to be associated with a lipid membrane are described in detail, in particular in documents U.S. Pat. No. 6,045,821, WO 90/04943 and WO 2006/100305. Depending on embodiments, the chelate carries a long lipophilic chain (phospholipid, for example) which is inserted into the membrane of the lipid nanoparticle (liposome, micelle, nanoemulsion). Similarly, the VCAM PEPTIDE advantageously carries a lipophilic chain (the Linker, for example a C$_{10}$ to C$_{20}$ alkyl chain) which is inserted into the membrane of the lipid nanoparticle.

According to advantageous embodiments, the lipid nanoparticle includes perfluorocarbons as described in U.S. Pat. No. 5,958,371, the liquid emulsion containing nanoparticles comprising a perfluorocarbon having quite a high boiling point (for example, between 50 and 90° C.), surrounded by a coating composed of a lipid and/or of a surfactant. The surfactant is capable of coupling directly to a targeting biovector or of including an intermediate compound covalently bonded to the biovector, where appropriate by means of a chemical bonding agent.

Various perfluorocarbon emulsions are recalled in document U.S. Pat. No. 6,676,963 (perfluorodecalin, perfluorooctane, perfluorodichlorooctane, perfluoro-n-octyl bromide, perfluoroheptane, perfluorodecane, perfluoro-cyclohexane, perfluoromorpholine, perfluorotri-propylamine, perfluorotributylamine, perfluorodimethyl-cyclohexane, perfluorotrimethylcyclohexane, perfluoro-dicyclohexyl ether, perfluoro-n-butyltetrahydrofuran).

As phospholipids forming the membrane of the nanoparticles, use is customarily made of the following compounds: phosphatidylcholine, dioleoylphosphatidyl-choline, dimyristoylphosphatidylcholine, dipalmitoyl-phosphatidylcholine, distearoylphosphatidylcholine, phosphatidylethanolamine.

Such compounds are described, for example, in U.S. Pat. No. 5,989,520 and U.S. Pat. No. 5,958,371, as recalled in document US 20040248856 which in particular cites perfluorocarbon compounds: perfluorodecalin, perfluorooctane, perfluorodichlorooctane, perfluoro-n-octyl bromide, perfluoroheptane, and the like.

According to advantageous embodiments, in order to prepare contrast agents according to the invention, use will be made of appropriate methods and lipid compositions recalled in U.S. Pat. No. 6,010,682, in particular as regards the detailed description of the lipid composition, and of the preparation of liposomes, of micelles and of emulsions.

It is recalled that emulsions are heterogeneous lipid mixtures obtained in an appropriate manner by mechanical stirring and/or addition of emulsifying agents. For example, the chelates rendered lipophilic are mixed mechanically with organic solvents such as chloroform. After the solvent has been evaporated off, the lipids are resuspended in an aqueous medium such as PBS, so as to obtain an emulsion which then typically undergoes sonication and microfluidization. The emulsions obtained can be lyophilized with, where appropriate, the use of anti-agglutination agents.

Typically, 1% to 75% by weight of lipophilic chelate compound, relative to the total ingredients of the emulsion, are used to formulate the desired paramagnetic contrast agent emulsion. The composition forming the contrast agent is preferably administered intravascularly, depending on the patient examined, for example at a rate of 0.1 mg to 1 g of lipophilic chelate compound and of 1 to 50 micromol of paramagnetic-metal ion per kg of patient.

The lipid compositions obtained are, where appropriate, formulated using additives recalled in U.S. Pat. No. 6,010,682, in particular for administration by intravenous injection. Mention will in particular be made of dextrose, sodium chloride and antimicrobial agents.

Advantageously, by virtue of the compositions according to the invention, an increase in relaxivity per ion can be obtained. The following characteristics, which can vary depending on the precise compositions of the emulsions and the method for the preparation thereof, are typically obtained:
  polydispersity index: 0.2 to 0.3
  [$Gd^{3+}$]=2 to 10 mM, preferably 3 to 7 mM
  particle concentration: 50 to 100 nm
  r1 ($mM^{-1}s^{-1}Gd^{-1}$): 5 to 40, preferably 10 to 40
  r2 ($mM^{-1}s^{-1}Gd^{-1}$): 20 to 40
  r1 ($mM^{-1}s^{-1}$ $particle^{-1}$): $10^6$ to $4\times10^6$
  number of biovectors: 50 to 1000, in particular 100 to 300.

The invention also relates to these compounds of formula (I) in which the Peptide contains a peptide sequence which has been modified, but without impairing the affinity and the specificity for the target and the effectiveness of the compound in vivo. The VCAM PEPTIDE is, for example, modified using appropriate methods described in the prior art, for example in US2005100963 (column 20-21, paragraphs [529] to [541] in the case of peptides targeting KDR receptors), in order to select effective compounds of formula (I):

1) substitution of amino acids without impairing their function, according to the method recalled in this document for hydrophobic amino acids, aromatic amino acids, acidic amino acids, amino acids containing hydroxyls, amino acids containing amide side chains. For lysine, use will also be made of other dibasic amino acids (arginine, histidine, ornithine) or derivatives of lysine or of these other amino acids, in particular the alkyl, alkenyl or aryl derivatives; such as N-epsilon-isopropyl lysine derivatives. The derivatives cited in paragraph of US2005100963 may in particular be tested;

2) substitution of amide bonds present on the backbone of the polypeptide, in particular so as to limit degradation of the peptide and/or to adjust the flexibility of the peptide (for example, insertion of alpha-N-methylamide or of a thioamide, replacement of an amino acid with an aza-amino acid);

3) introduction of D-series amino acids, such as D-alanine, in order to adjust the accessibility of the peptide for its target owing to an effect of steric modification on the orientation of the side chains;

4) chemical modifications in order to adjust the solubility and pharmacokinetics of the compound of formula (I), for example by adding a hydrophilic or basic group, or an alkyl or aromatic nonpolar group, by means of bonding to the C- or N-terminal part of the peptide, or to an amino acid side chain of the peptide, in particular to lysine which has a free amine function (or a derivative such as 2,3-diaminopropionic acid);

5) glycosylation;

6) other modifications:
  formation of salts: N-methylglucamine (meglumine), acetate, oxalates, ascorbates, etc.,
  manipulation of the peptide sequence (for example, retro-peptide or cyclization).

The biological tests described in detail in the application make it possible to select effective peptides which are equivalent or improved in terms of VCAM-targeting activity in comparison with the peptides exemplified in detail in the present application.

According to another aspect, the invention relates to the MRI contrast products comprising a compound of formula (I) as described above, the paramagnetic-metal M ion of which has the atomic number 21-29, 42-44 or 58 or 70, preferably gadolinium. The paramagnetic metals M include lanthanides having the atomic number 58-70 and transition metals having the atomic number 21-29, 42 or 44, for example scandium, titanium, vanadium, chromium, manganese, iron, cobalt, nickel, copper, molybdenum, ruthenium, cerium, praseodymium, neodymium, promethium, samarium, europium, gadolinium, terbium, dysprosium, holmium, erbium, thulium and ytterbium. The elements Gd(III), Mn(II), europium and dysprosium are particularly preferred; advantageously, M is chosen from Gd, Mn, Fe, Dy and Tm.

Advantageously, the Signal-Linker-Peptide compounds will be used for CEST (saturation transfer) imaging by integrating them into compounds of lipid particle type, such as liposomes (as described in detail in WO2006/032705). It is recalled that CEST imaging with or without lipid particles and with or without biovector can be carried out with chelates of value q=1 or of value q=2.

According to another aspect, the invention relates to the contrast products for X-ray or CT imaging, comprising a compound (I) as defined above, the heavy metal M ion of which has the atomic number 21-31, 39-50, 56-80, 82, 83 or 90.

According to another aspect, the invention relates to radiopharmaceutical products comprising a compound of formula (I) as described above, the chelate of which is coupled with a radionucleide or a radiohalogen known to those skilled in the art, typically gadolinium, technetium, chromium, gallium, indium, ytterbium, rhenium, lanthanum, yttrium, dysprosium, copper, or the like. The radionucleides include the radioactive forms of the elements Sm, Ho, Y, Pm, Gd, La, Lu, Yb, Sc, Pr, Tc, Re, Ru, Rh, Pd, Pt, Cu, Au, Ga, In, Sn, Cr, Pb, in particular $^{99}$Tc, $^{117}$Sn, $^{111}$In, $^{97}$Ru, $^{67}$Ga, $^{68}$Ga, $^{89}$Zr, $^{177}$Lu, $^{47}$Sc, $^{105}$Rh; $^{188}$Re, $^{60}$Cu, $^{62}$Cu, $^{64}$Cu, $^{67}$Cu, $^{90}$Y, $^{159}$Gd, $^{149}$Pr, $^{166}$Ho; advantageously $^{68}$Ga. The preparation of compounds that can be used as radiopharamaceuticals, in particular using technetium $^{99}$Tc, is summarized in US 2006/0018830, page 32, paragraph 4, these techniques being described in this document for compounds comprising a chelate coupled to a gastrin-targeting peptide.

For indications in radiotherapy, the coupling of macrocycles of DOTA type, the selection of appropriate nucleides, and the preparation of these radiotherapeutic compounds are summarized in US 2006/0018830, columns 35 and 36 (incorporated by way of reference).

According to another aspect, the invention relates to a method of diagnosis and a method of radiopharmaceutical treatment using a compound of formula (I) as described above.

The present invention also relates to a composition comprising at least one compound of general formula (I) as described above and a pharmaceutically acceptable excipient, advantageously for parenteral administration. In addition, it relates to a method for preparing such a composition, comprising the addition of a compound of general formula (I) as defined above to an injectable medium comprising the pharmaceutically acceptable excipient.

The invention relates to the use of a composition according to the present invention, for the diagnosis of a pathological condition associated with VCAM. The diagnostic and radiopharmaceutical compositions according to the invention can be used as described in applications US 2002/0090342, US 2002/0098149 and WO 02/055111 for anticancer indications. The invention in addition relates to the compounds of general formula (I) as defined above, for their use as an agent for diagnosing diseases associated with VCAM, advantageously chosen from cardiovascular diseases, risks of ischemic attack, chronic ulcerative colitis, Crohn's disease and/or cancer, advantageously from cardiovascular diseases and risks of ischemic attack.

Advantageously, the cardiovascular disease is chosen from: a disease associated with atheroma plaques, advantageously vulnerable plaques, and/or a coronary artery disease.

Advantageously, the risk of ischemic attack is chosen from: myocardial infarction, a cerebral stroke, a renal embolism, acute limb ischemia, and a ruptured aortic aneurysm.

The invention also relates to the use of the compounds described above, for the preparation of a diagnostic or radiopharmaceutical composition for use in the diagnosis and/or treatment of diseases associated with VCAM expression, advantageously chosen from cardiovascular diseases and/or risks of ischemic attack.

Where appropriate, the compounds of formula (I) and the VCAM peptides of the applicant will be used as a diagnostic agent, or as an agent for therapeutic treatment at the level of VCAM expression regions, or as a diagnostic and a therapeutic treatment agent, or an agent for diagnostic monitoring of therapeutic effectiveness. Where appropriate, the compound will be coadministered simultaneously, or after a delay, with other diagnostic and/or therapeutic agents targeting VCAM expression regions. The invention also relates to a method comprising the synthesis of a compound comprising a paramagnetic metal according to the invention, capable of targeting a pathological region, its administration to a patient, and imaging by MRI. The invention also relates to a method of diagnosis comprising the synthesis of a radiopharmaceutical compound according to the invention, capable of targeting a pathological region, its administration to a patient, and imaging by SPECT or planar gamma scintigraphy, or positron emission tomography.

For a diagnosis by MRI, the intravenous administration by injection, usually in a saline solution, is typically carried out at a dose of metal ion of from 0.001 to 1.5 mmol/kg of body weight, for example from 1 to 500 µmol Gd/kg.

For a radiopharmaceutical diagnosis, the intravenous administration by injection, usually in a saline solution, is typically carried out at a dose of from 1 to 100 mCi per 70 kg of body weight, preferably from 5 to 50 mCi, with diagnostic imaging, for example, 30 to 180 minutes after the injection for $^{99}$Tc.

For use as X-ray contrast agents, the concentration of heavy atom is typically from 0.1 M to 5 M, with concentrations per intravenous administration of the order of 0.5 to 1.5 mmol/kg.

According to another aspect, the invention relates to the use of a compound (I) as described above, for the preparation of a composition for use in optical imaging.

Examples of administration of compositions for medical imaging are described in the prior art, for example in documents WO 02/26776 and US 2006/0018830, column 36 ([0282]), paragraph 8 (dosages and additives).

Pharmaceutically, physiologically acceptable carriers for forming diagnostic compositions (contrast products) comprising the compounds described above are known in the prior art. Salts (sodium, calcium, meglumine), pH regulators (acetic acid, citric acid, fumaric acid) and antioxidants will, for example, be used.

The invention also relates to a method for preparing compounds, comprising the coupling of a VCAM PEPTIDE with at least one chelate. Several general methods for preparing compounds of formula (I), described in US2006/0018830 (Bracco) are applicable, with a Peptide being used in place of the peptides of these documents. These methods, selected as a function in particular of the selected chelate, are recalled in 2006/0018830, column 37 ([0288] to [0291]) ("general preparation of compounds" and "alternative preparation of the compounds via segment coupling"), for example the SPPS and FMOC (9-fluorenylmethyl carbamate) methods.

The invention also relates to a method of radiopharmaceutical treatment or diagnosis, which comprises administering a compound (I), carrying out an imaging examination using appropriate equipment, and analyzing the results.

Unless otherwise indicated, the invention covers all the chiral, diastereoisomeric and racemic forms, in particular cis-trans forms, and L-D forms of the compounds described.

The applicant has also studied the possibilities of association of a VCAM PEPTIDE coupled to several chelates in the compound of formula (I). The applicant has, moreover, studied compounds of formula (I) exhibiting an assembly between one or more VCAM-targeting Peptides of the compound of formula (I) and one or more chelates, in such a way that access to the target is not hindered despite the presence of the chelate(s). For example, the chelate is distanced from the PEPTIDE(S) P by the Linker which is of sufficient size and has a chemical structure such that the recognition of the peptide(s) by their target is not impaired.

Among the biovector (peptides or optional other biovectors)/chelate associations, mention may in particular be made of:

a central biovector peptide linked to several chelates which may be identical or different;

a central chelate linked to several peptides which may be identical or different;

a first [peptide carrying chelate(s)] assembly coupled by means of a hydrophobic or hydrophilic linker to a second [peptide carrying chelate(s)] assembly, which is written, for example:

Ch1-peptide1-Linker-peptide2-Ch2 with Ch representing chelates which may be identical or different, and peptide1 and peptide2 representing Peptides which may be identical or different;

a peptide1-(Linker carrying Ch)-peptide2-Ch assembly.

Use will, for example, be made of the method of constructing multimeric compounds described in US2005/0100963 (WO2006/031885, page 66, line 25 to page 69, line 30) in the case of peptides targeting KDR receptors (for example using method 13 of the examples: "preparation of homodimers and heterodimers"), but using the VCAM PEPTIDE (the peptides of the compounds of FIGS. 44 to 47 of US2005100963 will, for example, be replaced with VCAM PEPTIDES). The compound may thus advantageously comprise a peptide coupled to several chelates, or a chelate coupled to several peptides, which may be identical or different. The invention also relates to mixed compounds comprising, in addition to the VCAM PEPTIDE, at least one other VCAM-targeting biovector, the biovector being either another peptide or another biovector, but which is a non-peptide biovector.

Where appropriate, the peptide portion or the chelate portion may be coupled to chemical groups for promoting the biodistribution or the lifetime of the product in the blood.

The specificity of the product refers to its specific affinity for at least one marker for VCAM or for any associated pathological disorder, the binding specificity being expressed typically by Kd and Ka constants, the Kd value for the target markers being less than 10 µM, preferably less than 1 µM.

Among the pharmaceutically acceptable salts, mention will in particular be made of salts of cations of inorganic bases (potassium, sodium, calcium, magnesium, etc.), of cations of organic bases (ethanolamine, diethanolamine, morpholine, glucamine, N-methylglucamine, N,N-dimethylglucamine, etc.), of anions of inorganic acids (in particular chlorides, bromides, iodides, sulfates, etc.), of anions of organic acids (acetate, succinate, citrate, fumarate, maleate, oxalate, trifluoroacetate, etc.), and of ions of amino acids (taurine, glycine, lysine, arginine, ornithine, aspartic acid, glutamic acid, etc.).

The invention also relates to the use of a VCAM PEPTIDE for an in vitro diagnosis (assaying of soluble VCAM-1 in blood plasma) and for anti-inflammatory therapy (multimerization of the peptide may increase its effectiveness via the polyvalence effect).

DEFINITIONS

The definitions of pathological conditions, the diagnosis of which is the subject of the present invention, which are disclosed in document WO200603788, are reiterated herein.

The term "VCAM-targeting peptide" or "VCAM PEPTIDE" denotes a molecule capable of binding selectively to VCAM (more especially VCAM-1).

The term "cardiovascular disease" includes in particular the states marking the development of a plaque and the complications resulting from the formation of an atheroma plaque (stenosis, ischemia) and/or from its progression to an acute ischemic attack (thrombosis, embolism, infarction, ruptured artery). The cardiovascular diseases denote, for example, atherosclerosis, an atheroma plaque, in particular vulnerable plaque, coronary artery disease, angina, thrombosis, cerebral stroke, myocardial infarction, vascular stenosis, infarction.

"Coronary artery disease" is the most common manifestation of cardiovascular disease. It is a progressive disease, due to poor irrigation of the cardiac muscle, subsequent to narrowing (stenosis) or to calcification (sclerosis) of one or more coronary arteries. The main symptom of coronary artery disease manifests itself in the form of pain which constitutes angina (stable or unstable), also known as angina pectoris. Complete obstruction of one or more coronary arteries results in infarction.

The term "infarction" denotes a confined seat of necrosis due to an arterial obstruction. More specifically, myocardial infarction is necrosis of the myocardium, which is generally the result of an acute coronary thrombosis secondary to plaque rupture (generally an unstable plaque or vulnerable plaque) leading to platelet aggregation and then coronary occlusion.

The term "thrombosis" corresponds to clotting of the blood in the vascular cavities (arteries, veins, capillaries or cardiac cavities) resulting in the formation of a thrombus.

"Embolism" is the intravascular migration of a foreign body, most commonly made up of a blood clot (thrombus), and its abrupt arrest in a vessel of insufficient caliber to allow it to pass. The local consequences of the embolism are circulatory disturbances related to the vascular obstruction, most commonly resulting in an infarction.

The term "ischemia" denotes a decrease in arterial blood supply in an area of the body. Its principal local causes are thrombosis and embolism.

The expression "vulnerable plaque" denotes an atheroma plaque having a fine fibrous shell (approximately 65 to 150 µm thick) and a large lipid core. These unstable plaques, which have a tendency to rupture, are encountered in the coronary arteries and in the aorta and its branches. The rupturing of vulnerable coronary plaques causes "acute coronary syndromes": in the event of complete occlusive thrombosis, the syndrome is myocardial infarction; when the thrombosis of the artery remains incomplete, the syndrome is unstable angina. In the corotid, the vulnerable plaques are more stenotic and less inflammatory. They also express VCAM-1.

In the present application, the following correspondence table is used.

| | | |
|---|---|---|
| Alanine | A | Ala |
| Arginine | R | Arg |
| Asparagine | N | Asn |
| Aspartate | D | Asp |
| Cysteine | C | Cys |
| Glutamate | E | Glu |
| Glutamine | Q | Gln |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

As illustrated below, the applicant has demonstrated in particular the effectiveness of products of MRI comprising a chelate linked to the VCAM PEPTIDE, in particular NNSKSHT (SEQ ID NO: 3).

Thus, even if a peptide was known from the prior art, the identification of its usefulness in a mechanism for targeting VCAM, in particular VCAM-1, among the extremely large number of possible biological targets, is far from evident. Furthermore, it is in no way evident that this identified biological target of the coupled compounds (VCAM PEPTIDE-signal entity) will make it possible to solve the technical problems solved by the applicant, in particular:

- the conservation of the in vivo affinity for the biological recognition site, despite the steric hindrance and the possible conformational modification in vivo owing to the coupling to a signal entity;
- the possibility of chemical coupling with the signal entities; the coupling with the PCTA derivatives in particular has meant that a dedicated chemical synthesis has had to be developed;
- the in vivo physicochemical stability which constitutes a major limitation for many peptides;
- the ability to be recognized in imaging in vivo, in particular in MRI, a technique in which the level of sensitivity is close to 1000 times lower than PET imaging.

Overall, it was therefore absolutely not obvious, for those skilled in the art:

- on the one hand, to select the peptides which are the subject of the present invention,
- on the other hand, for the products integrating these peptides to be actually effective in vivo.

In the detailed description which follows, a description is given of peptides for which the effectiveness has been shown with variant embodiments on various signal entities (PART I) and the biological results (PART II).

BRIEF DESCRIPTION OF DRAWINGS

FIG. 1 illustrates the calculation of the Kd* (apparent dissociation constant) value for VCAM-1.

FIG. 2 represents the measurement of the affinity of the peptide NNSKSHT (SEQ ID No. 3) (inhibitary constant-50 or $IC_{50}$ evaluated).

FIGS. 3 and 4 illustrate the enhancement, in MRI, of a DOTA-NNSKSHT product.

FIG. 5 shows MRI images on an ApoE/c mouse, obtained with a DOTA-NNSKSHT product.

EXAMPLES

Part I

Preparation of the Compounds Including VCAM PEPTIDES

General Information

M: molar concentration (mol/l).

M/z: mass-to-charge ratio determined by mass spectrometry.

$ES^+$: positive mode electrospray.

$ES^-$: negative mode electrospray.

kDa: unit of molecular mass (kiloDalton).

TLC: Thin Layer Chromatography.

Zave: hydrodynamic diameter measured by PCS.

Assaying of Total Iron:

The iron is assayed by atomic absorption spectroscopy (VARIAN AA10 spectrophotometer) after mineralization with concentrated HCl and dilutation relative to a standard range of ferric ions (0, 5, 10, 15 and 20 ppm).

Particle Size:

Hydrodynamic Diameter of the Grafted Particle (Zave):

Determined by PCS (Malvern 4700 instrument, laser 488 nm at 90°) on a sample diluted to ~1 millimolar with water for injectable preparation, filtered through 0.22 μm.

PCS=Photon Correlation Spectroscopy=Technique by dynamic light scattering—Reference: R. Pecora in *J. of Nano. Res*. (2000), 2, p. 123-131.

Structural Analyses:

By mass spectroscopy (Micromass VG Quattro II instrument) with an electrospray source.

Relaxivity Measurements:

The relaxation times T1 and T2 were determined by standard procedures on a Minispec 120 instrument (Bruker) at 20 MHz (0.47 T) and 37° C. The longitudinal relaxation time T1 is measured using an inversion-recovery sequence and the transverse relaxation time T2 is measured using a CPMG technique.

The relaxation rates R1 (=1/T1) and R2 (=1/T2) were calculated for various concentrations of total metal (ranging from $0.1\times10^{-3}$ to $1\times10^{-3}$ mol/l) in an aqueous solution at 37° C. The correlation between R1 or R2 as a function of the concentration is linear, and the slope represents the relaxivity r1 (R1/C) or r2 (R2/C) expressed as (1/second)×(1/mmol/l), i.e. ($s^{-1}\cdot mM^{-1}$)

The nanoparticles were prepared according to the methods described in patent WO 2004/058275 (US 2004/253181), examples 8 and 9 for the preparation of colloidal solutions of magnetic particles, and examples 10 to 12 for the complexation of the magnetic particles with a gem-bisphosphonate coating of example 1 of WO 2004/058275.

Example 1

Coupling of the Peptides to the Particle of Iron Oxide (Product PEG-USPIO-VCAM PEPTIDE)

The peptide sequences of interest are given in the table below:

| No. | Code | Peptide | Sequence |
|---|---|---|---|
| 1 | COMPOUND A (peptide CNNSKSHTC, Linker L of squarate type) | 8-amino-3,6-dioxaoctanoyl-cyclo-[Cys-Asn-Asn-Ser-Lys-Ser-His-Thr-Cys]-OH | CNNSKSHTC (SEQ ID No. 2) |
| 2 | COMPOUND B (compound A with mixed sequence) | 8-amino-3,6-dioxaoctanoyl-His-Ser-cyclo-[Cys-Asn-Lys-Asn-Ser-Cys]-Thr-OH | HSCNKNSCT (SEQ ID NO: 6) |

-continued

| No. | Code | Peptide | Sequence |
|---|---|---|---|
| 3 | COMPOUND C | 8-amino-3,6-dioxaoctanoyl-cyclo-[Cys-Met-Lys-Thr-Asp-Thr-Arg-Leu-Cys]-OH | CMKTDTRLC (SEQ ID No. 5) |

Coupling of Peptide No. 1 to a Particle of Iron Oxide Protocols:

| No. | Code | Peptide | Mass involved |
|---|---|---|---|
| 1 | COMPOUND A | 8-amino-3,6-dioxaoctanoyl-cyclo-[Cys-Asn-Asn-Ser-Lys(tfa)-Ser-His-Thr-Cys]-OH | 20 mg |

Coupling:

15 ml of nanoparticles ([Fe]=0.338 M) are stirred at ambient temperature, the pH is equal to 7.2. A solution of the protected peptide (No. 1, -Lys(tfa)-, 20 mg) in 1 ml of water is added in portions of 100 µl with 2.25 mg of EDCI every 15 minutes. Once the addition is complete, the solution is stirred overnight. The pH is adjusted to 7 with a 0.1 M NaOH solution.

The solution is then filtered through 0.22 µm (Millipore® Durapore filter) and ultrafiltered through a 30 kDa membrane, and then concentrated to a final volume of 15 ml.

Coupling of PEG:

2.5 ml of a solution of 1.060 g of amino-PEG (O-(2-aminoethyl)-O'-methylpolyethylene glycol 750, Aldrich, R N [80506-64-5]) in 5 ml of water are added to 15 ml of the above solution. The pH of the solution is adjusted to 8 with 1M HCl, and then 0.325 g of EDCI is added and the mixture is stirred for 3 h. The addition of the amino-PEG solution (2.5 ml) and of EDCI (0.325 g) is repeated once and the mixture is stirred at ambient temperature overnight. The pH is brought back to 7.5 with 1M HCl. The solution is filtered through 0.22 µm and ultrafiltered through a 30 kDa membrane. The final volume of solution is 15 ml.

Deprotection:

The solution is adjusted to pH 10.1 with 1M NaOH and stirred at ambient temperature for 6 h. The pH is then brought back to 7.5 with 1M HCl and the solution is filtered through 0.22µ and ultrafiltered through a membrane with a cutoff threshold of 12 kDa.

Characterization: PCS: Zave=26 nm
Iron concentration: 137.61 mM
$r_1$ (20 MHz, 37° C.): 30.54 $s^{-1}mM^{-1}$
$r_2$ (20 MHz, 37° C.): 76 $s^{-1}mM^{-1}$
$r_1$ (60 MHz, 37° C.): 14.94 $s^{-1}mM^{-1}$
$r_2$ (60 MHz, 37° C.): 85.06 $s^{-1}mM^{-1}$

| Samples | Magnetic diameter | Saturation magnetization (magn.) | Relax. diameter | Saturation magnetization (relax.) |
|---|---|---|---|---|
| PEG750-COMPOUND A | 9.94 nm | 63.1 $Am^2/kg$ | 11.2 nm | 48.9 $Am^2/kg$ |

The same protocol was followed for obtaining the other products.

Coupling of Peptide No. 2 to a Particle of Iron Oxide

| No. | Code | Peptide | Mass involved |
|---|---|---|---|
| 2 | COMPOUND B | 8-amino-3,6-dioxaoctanoyl-His-Ser-cyclo-[Cys-Asn-Lys(tfa)-Asn-Ser-Cys]-Thr-OH | 20 mg |

Characterization:
PCS: Zave=29 nm
Iron concentration: 118.60 mM
$r_1$ (20 MHz, 37° C.): 31.34 $s^{-1}mM^{-1}$
$r_2$ (20 MHz, 37° C.): 79.61 $s^{-1}$ $mM^{-1}$
$r_1$ (60 MHz, 37° C.): 14.30 $s^{-1}mM^{-1}$
$r_2$ (60 MHz, 37° C.): 78.05 $s^{-1}$ $mM^{-1}$ Example 2

Coupling of the Peptides to Gadolinium Chelates

General Scheme:

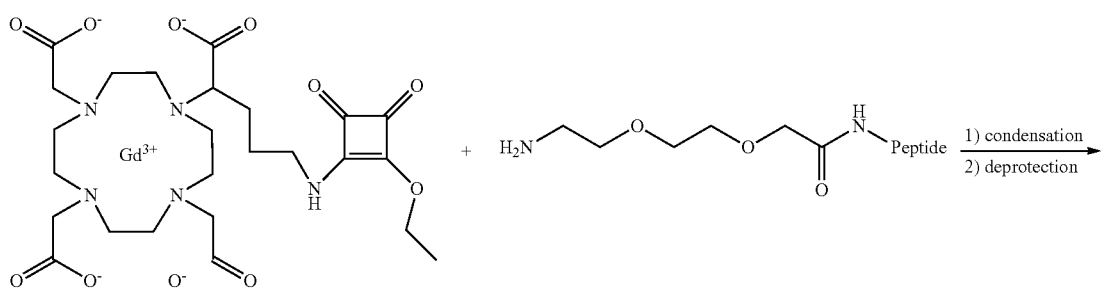

Gd-DOTA-EthylSquarate

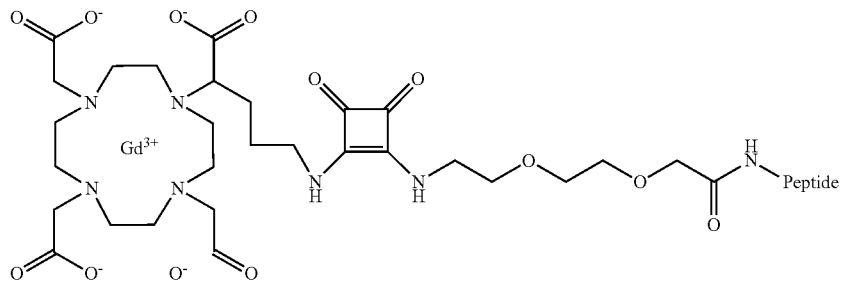

Sequence of the Coupled Peptides:

| No. | Code | Peptide | Sequence |
|---|---|---|---|
| 1 | COMPOUND A | 8-amino-3,6-dioxaoctanoyl-cyclo-[Cys-Asn-Asn-Ser-Lys-Ser-His-Thr-Cys]-OH | CNNSKSHTC (SEQ ID No. 2) |
| 2 | COMPOUND B | 8-amino-3,6-dioxaoctanoyl-His-Ser-cyclo-[Cys-Asn-Lys-Asn-Ser-Cys]-Thr-OH | HSCNKNSCT (SEQ ID NO: 6) |
| 3 | COMPOUND C | 8-amino-3,6-dioxaoctanoyl-cyclo-[Cys-Met-Lys-Thr-Asp-Thr-Arg-Leu-Cys]-OH | CMKTDTRLC (SEQ ID No. 5) |

Condensation, Deprotection:

210 mg of Gd-DOTA-diethylsquarate (prepared according to the protocol given in detail in example 3) are dissolved in 20 ml of water. The pH is adjusted to 9 with a saturated solution of $Na_2CO_3$. 350 mg of protected peptide No. 1 (-Lys(tfa)-) are added and the pH is adjusted to 9.2. The mixture is left to react for 4 days. The solution is dialyzed through membranes with a cutoff threshold of 1000 Da for 48 h and then chromatographed on an RP-18 column (eluant: MeOH/water (50/50)).

Peptides Nos. 2 and 3 are condensed according to the same procedure.

The products obtained have the following structure:

| No. | Structure | MW | Mass spectro. |
|---|---|---|---|
| 4 | 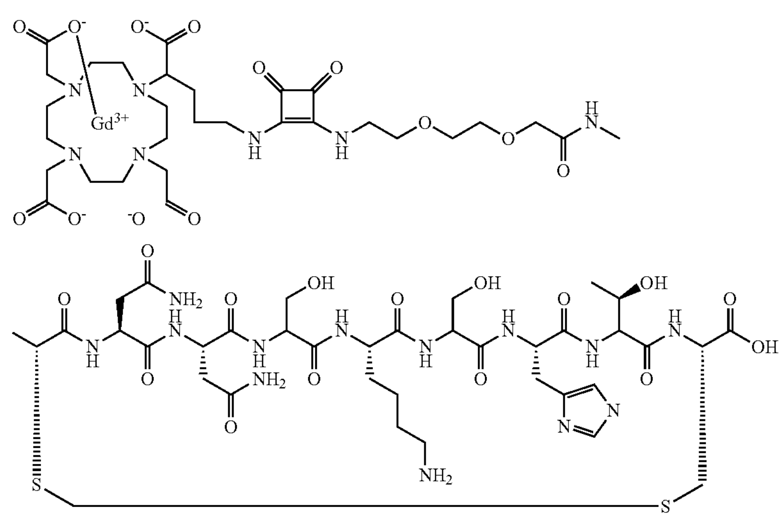 | 1829.0 | complies |

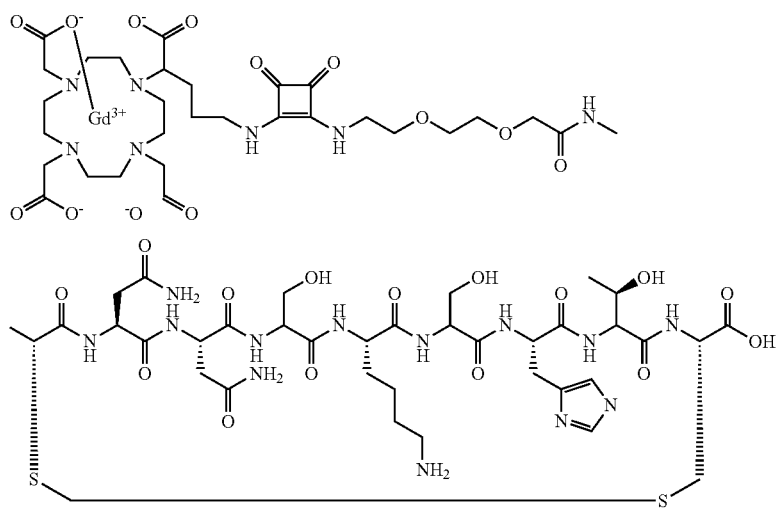

-continued
| No. | Structure | MW | Mass spectro. |
|---|---|---|---|
| 5 | 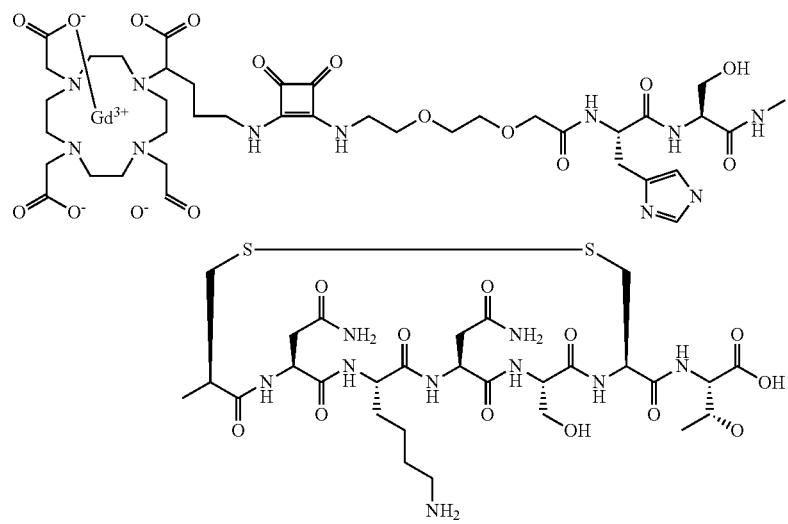 | 1829.0 | complies |
| 6 | 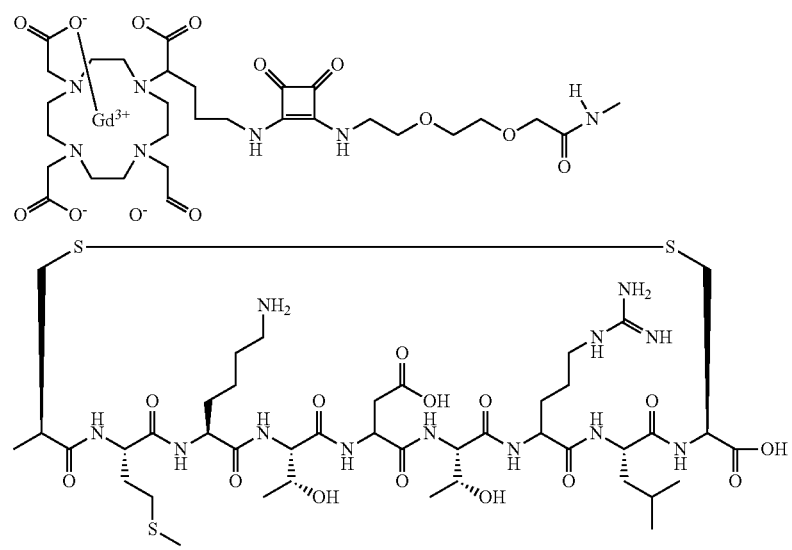 | 1906.23 | complies |

Example 3

Synthesis of a DOTA-Derived Bifunctional chelate

Stage 1: 5-(1,3-dioxo-1,3-dihydroisoindol-2-yl)-2-(1,4,7,10-tetraazacyclododec-1-yl)pentanoic acid benzyl ester

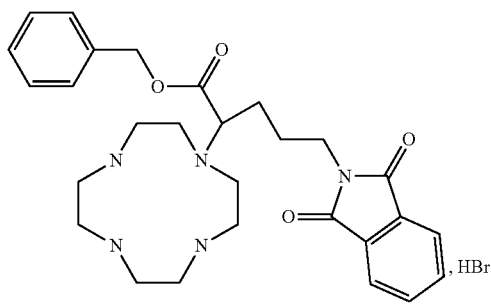 [SMILES: O=C(OCc1ccccc1)C(CCCN1C(=O)c2ccccc2C1=O)N1CCNCCNCCNCC1]

55 g of cyclen base (320 mmol) are dissolved in 550 ml of CH$_3$CN, to which 119.8 g of brominated derivative (2-bromo-5-(1,3-dioxo-1,3-dihydroisoindol-2-yl)pentanoic acid benzyl ester, 288 mmol) dissolved in 550 ml of CH$_3$CN are added dropwise. The medium is stirred at ambient temperature overnight. The precipitate is filtered off and washed thoroughly with acetonitrile. 138 g of product are obtained in the form of a white powder (corrected yield 81.3%).
TLC: CH$_2$Cl$_2$/MeOH/NH$_4$OH at 25% (80/40/3)
Revelation UV and CuSO$_4$
Rf: 0.3.

Stage 2: 5-(1,3-dioxo-1,3-dihydroisoindol-2-yl)-2-(4,7,10-tris(ethoxycarbonylmethyl)-1,4,7,10-tetraazacyclododec-1-yl)pentanoic acid benzyl ester

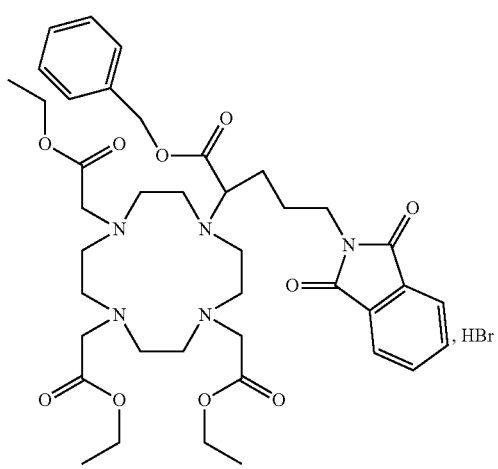 [SMILES: CCOC(=O)CN1CCN(CC(=O)OCC)CCN(C(CCCN2C(=O)c3ccccc3C2=O)C(=O)OCc2ccccc2)CCN(CC(=O)OCC)CC1]

60 g of the compound obtained in stage 1 (102 mmol) and 50.1 g of Na$_2$CO$_3$ (464 mmol) are added to a solution of 59.1 g of ethyl bromoacetate (Aldrich®, 358 mmol) in CH$_3$CN (1.1 l). The reaction medium is heated at 80° C. under a covering of argon overnight. After removal of the precipitate, the filtrate is concentrated and washed thoroughly with CH$_3$CN. The product is crystallized from CH$_3$CN by dropwise addition of Et$_2$O. 89.8 g of product are obtained in the form of a white solid (corrected yield 100%).
TLC: CH$_2$Cl$_2$/MeOH (9/1)
Revelation UV and KMnO$_4$; Rf: 0.4.

Stage 3: 5-amino-2-(4,7,10-tris(carboxymethyl)-1,4,7,10-tetraazacyclodedec-1-yl)pentanoic Acid

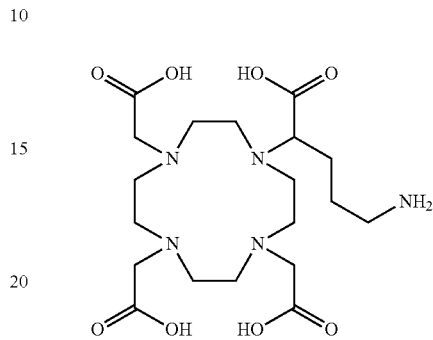

In a 5-liter reactor, a solution of 54 g of compound obtained in stage 2 (64 mmol) in 37% hydrochloric acid (1.8 l) is refluxed overnight. After cooling and filtration, the filtrate is concentrated and purified on silanized silica (elution with water). After evaporation under reduced pressure, the product is washed with ether. 45 g of product are obtained in the form of a white solid. The product is desalified by passing it over OH$^-$ resin. 30 g of product are isolated in the form of white crystals (yield 100%).
HPLC: Hypercarb® 5μ, 200×4.6, 250 Å; solvent A: 0.037 N sulfuric acid
Solvent B: CH$_3$CN: UV detection at 201 nm; Tr: 18 min.

Stage 4: 5-amino-2-(4,7,10-tris(carboxymethyl)-1,4,7,10-tetraazacyclododec-1-yl)pentanoic acid gadolinium complex

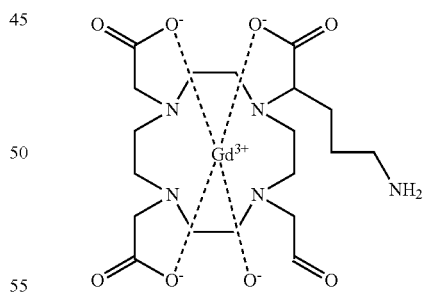

7.2 g of the compound obtained in stage 3 (16 mmol) are dissolved in 70 ml of water and the pH is adjusted to 5.5 by adding 6N hydrochloric acid. 2.9 g of Gd$_2$O$_3$ (8 mmol) are added and the reaction medium is heated at 80° C. The pH of the solution increases steadily, and should be maintained between 5.2 and 5.7 by dropwise addition of 6N hydrochloric acid. After two hours, the pH stabilizes at 5.7. The slight cloudiness is filtered out through a Whatman® filter and the filtrate is concentrated. 11.1 g of product are obtained in the form of white flakes (corrected yield 100%).

HPLC: Hypercarb® 5µ, 200×4.6, 250 Å; solvent A: 0.037 N sulfuric acid
Solvent B: CH$_3$CN: UV detection at 201 nm; Tr: 10 min.

Stage 5: 5-(2-ethoxy-3,4-dioxocyclobut-1-eny-lamino)-2-(4,7,10-tris(carboxymethyl)-1,4,7,10-tetraazacyclododec-1-yl)pentanoic acid gadolinium complex

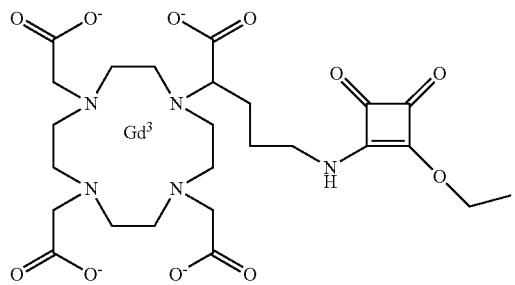 [SMILES: CCOc1c(NCCCC(C(=O)[O-])N2CCN(CC(=O)[O-])CCN(CC(=O)[O-])CCN(CC(=O)[O-])CC2)c(=O)c1=O]

8 g of compound obtained in stage 4 are dried by azeotropic distillation with toluene, and then suspended in 90 ml of anhydrous DMSO under a covering of argon. 2.8 ml of screen-dried Et$_3$N (1.7 eq.) and 5 g of diethyl squarate (Aldrich®, 2.5 eq.) are subsequently added. The medium is stirred at ambient temperature under a covering of argon for 1 hours. The mixture is precipitated from 600 ml of ether. The solid obtained is filtered and then washed with dichloromethane. After filtration and drying, 7.5 g of a white solid (yield of 81.5%) are recovered.
HPLC: Symmetry C18, 5µ, 250×4.6, 100 Å
A: Water with TFA, pH=2.7; B: CH$_3$CN: Detection at 201 and 254 nm; Tr: 19.8 min.

EXAMPLES

Part II: Demonstration of the Effectiveness of VCAM PEPTIDES

Throughout PART II which follows and also the associated figures, the cyclic peptide CNNSKSHTC (SEQ ID No. 2) is written in the form NNSKSHT (SEQ ID No. 3) which shows the sequence.
II.1 Peptide NNSKSHT (SEQ ID No. 3)
The interaction between the peptide and VCAM-1 is evaluated by means of an ELISA assay. The peptide NNSKSHT (SEQ ID No. 3) is immobilized on a plate at the concentration of 50 µg/ml (3 µg/weld) overnight at 4° C. The nonspecific sites are then saturated in a BSA-enriched buffer for 2 hours at 4° C. After several rinses, the VCAM-1 molecule (recombinant human VCAM-1/Fc chimera) is incubated at increasing concentrations ($3.9 \times 10^{-9} - 4.9 \times 10^{-7}$ M) for 2 hours at ambient temperature. The VCAM-1 protein bound to the peptide is detected through the addition of a solution of mouse antihuman VCAM-1 monoclonal antibody diluted to 1/500 in TBS buffer. The incubation is sustained for 1 hour at ambient temperature. After removal of the unbound antibodies, the revelation is carried out by addition of a peroxydase-conjugated anti-mouse IgG antibody (secondary antibody) diluted to 1/200 in a phosphate buffer (1 hour at 4° C.) and of a solution of ABTS substrate enriched in H$_2$O$_2$. Measurement of the OD at 405 nm makes it possible to calculate the K*$_d$ value of VCAM-1.

The affinity of the peptide for VCAM-1 is directly calculated from a functional cell assay which consists in measuring the inhibition of cell adhesion. The VCAM-1 protein is immobilized on an ELISA plate at the concentration of 20 µg/ml (1.2 µg/well) overnight at 4° C. The peptide NNSKSHT (SEQ ID No. 3) is then preincubated at increasing concentrations for 1 hour at ambient temperature. After washing, Jurkat cells, prestimulated with 50 ng/ml of PMA for 3 hours, are incubated ($10^5$ cells/weld) for 1 hour at ambient temperature. After several rinses, the cells bound to the VCAM-1 are fixed in a 1% glutaraldehyde solution (45 minutes at 4° C.). After washing, a 1% cresyl violet solution is incubated for 30 minutes. The wells are again rinsed, and then incubated overnight at ambient temperature with a solution of ethanol. The blue coloration of the adherence cells makes it possible to measure the OD at 630 nm. The inhibition of cell adhesion by the peptide NNSKSHT (SEQ ID No. 3) makes it possible to calculate an IC$_{50}$ value.
II.2. Gd-DOTA-NNSKSHT contrast product
The peptide NNSKSHT (SEQ ID No. 3) protected with TFA is coupled to DOTA. The lysines are deprotected once the coupling has been carried out.
Before the MRI acquisition, the mice are anesthetized with pentobarbital. All the experiments are carried out on a 200 MHz Bruker spectrometer (4.7 T) equipped with a vertical magnet and with a microimaging system.
The contrast products are tested on two different models.
II.2.1 Test on a Model of Concanavalin-A (Con-A)-induced hepatitis in mice
The hepatitis is induced by i.v. injection of 20 mg/kg of Con-A in Balb/c mice weighing approximately 26 g. The literature reports that VCAM-1 is massively expressed in the liver between 4 and 8 hours after the injection of Con-A. The MRI protocol is the following: (1) the precontrast MRI begins 4h30 after the injection of Con-A; (2) the contrast product is injected at the dose of 100 µmol Gd/kg approximately 5 h after the injection of Con-A; (3) several post-contrast acquisitions are carried out for 1 h30 every 7 minutes. The images are acquired using an MSME (multi-slice-multi-echo) sequence, the parameters of which are the following: TR/TE=307.4/14.7 ms, matrix=256, FOV=5 cm, slice thickness=3 mm, eight axial slices (which completely cover the abdominal region including the kidneys), TA=5 minutes 14 seconds.
II.2.2. Test on a model of atherosclerosis in the apoE$^{-/-}$ mouse
Female C57B16 ApoE$^{-/-}$ mice approximately 15 months old are subjected to a cholesterol-rich diet for 3 months before the MRI studies. For the acquisition by MRI, the animals are anesthetized. The Gd-DOTA-NNSKSHT contrast agent is injected at the dose of 100 µmol Gd/kg. All the images are acquired at the level of the abdominal aorta, in particular the region close to the kidney, which is known for the development of atheroma plaques owing to the presence of the arterial branches.
The images are acquired using two sequences:
MSME (multi-slice-multi-echo) with the following parameters: TR/TE=695.8/8.9 ms, NEX=2, spectrum width=50 kHz, matrix=256×256, FOV=2.3×2.3 cm, slice thickness=1 mm, 20 axial slices, spatial resolution=90×90 µm, TA=5 minutes 56 seconds.
The parameters of the RARE (rapid acquisition with relaxation enhancement) sequence are adjusted using a reference tube filled with a 1 mM solution of Gd-DOTA. The image acquisition parameters are the following: TR=470.9-1048.5 ms, TE=4 ms, RARE factor=1-4, NEX=4, matrix=256×256, FOV=2.3 cm, spectral width=33.33 kHz, slice thickness=0.8 mm, spatial resolution=90 μm.

II.2.3. Signal Processing

For the two models, the SI values are measured in various regions of interest (at the level of the arterial wall of the abdominal aorta or whole liver) using the OSIRIS image analysis software. The regions are first drawn on the post-contrast images, and then duplicated on the pre-contrast images. The SI value is measured on all the image slices where the arterial wall and the liver are visible. Finally, the SI values obtained for serial slices of aorta over a length of 3.2-8 mm are averaged for each animal. The increase in the signal/noise ratio (% ΔSNR) is calculated according to the following equation:

% ΔSNR=[($SI_{post}/SD_{noise}$)−($SI_{pre}/SD_{noise}$)]/[$SI_{pre}/SD_{noise}$]×100 where $SD_{noise}$ is the standard deviation of the noise measured on a region outside the animal.

REFERENCES

Wolf D, Hallmann R, Sass G, Sixt M, Küsters S, Fregien B, Trautwein C and Tiegs G (2001) TNF-α-induced expression of adhesion molecules in the liver is under the control of TNFR1—relevance for concanavalin A-induced hepatitis 1, *J. Immunol.* 166: 1300-1307. Burtea C, Laurent S, Vander Elst L, Toubeau G and Muller R N (2006) Molecular imaging of angiogenic blood vessels in vulnerable atherosclerotic plaques with a mimetic of RGD peptide grafted to Gd-DTPA, ESMRMB (Annual Meeting of the European Society of Magnetic Resonance in Medicine and Biology), Warsaw, Poland.

II.3 Results

II.3.1 Peptide NNSKSHT (SEQ ID No. 3)

The ELISA assay (FIG. 1) based on the immobilization of the peptide NNSKSHT (SEQ ID No. 3) in the presence of increasing concentrations of VCAM-1 makes it possible to calculate an apparent dissociation constant value $K^*_d$ (VCAM-1) equal to $1.35 \times 10^{-7}$ M, thereby demonstrating good interaction between the peptide and the VCAM-1 molecule.

Figure 2:
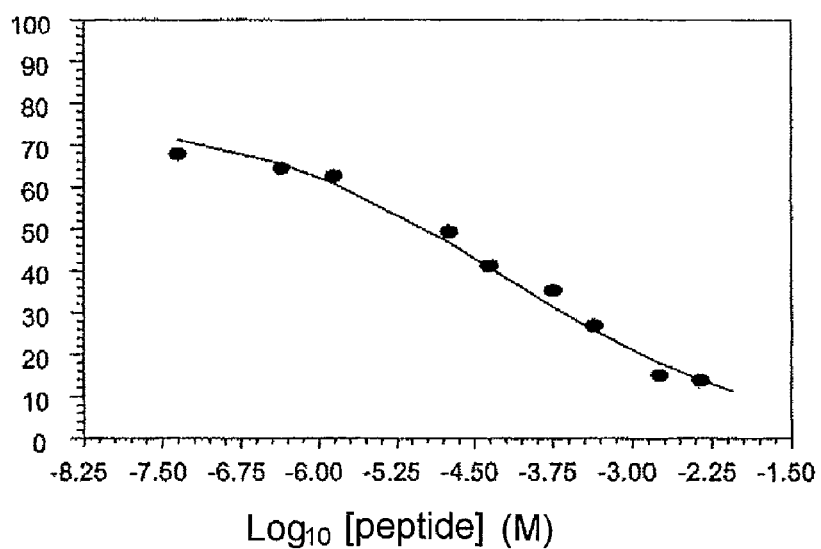

The functional assay for inhibition of cell adhesion by the peptide NNSKSHT (SEQ ID No. 3) (FIG. 2) makes it possible to calculate an $IC_{50}$ value (peptide) equal to $6.3 \times 10^{-5}$ M, thereby attesting to the specific interaction between the peptide and VCAM-1.

II.3.2 Gd-DOTA-NNSKSHT Contrast Product

II.3.2.1. MRI In Vivo on a Model of Con-A-Induced Hepatitis in Mice

The change in the signal/noise ratio (% ΔSNR) over time shows that the i.v. injection of Gd-DOTA-NNSKSHT induces a greater enhancement of the MRI signal in the hepatitis model compared with the liver in the healthy mouse. The kinetic profiles of the ΔSNRs are substantially identical in the mouse suffering from hepatitis and in the healthy mouse after injection of 100 μmol Gd/kg of Gd-DOTA. The signal recorded after injection of Gd-DOTA-NNSKSHT in the mouse suffering from hepatitis is greater from the first minutes of acquisition onward and is maintained for longer (at least 70 minutes) than the signals recorded in the healthy mouse or those acquired after injection of Gd-DOTA (decrease in the signal from the 10th minute onward for the three conditions).

Figure 3:
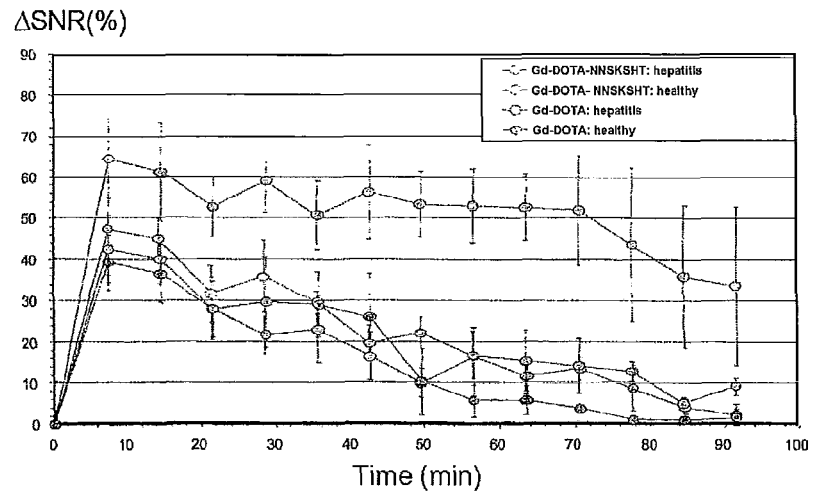

(FIG. 3: monitoring over time of the targeting of the liver in healthy mice or mice suffering from Con-A-induced hepatitis (n=6) after i.v. injection of 100 μmol Gd/kg of Gd-DOTA or Gd-DOTA-NNSKSHT).

These results demonstrate that the grafting of the peptide NNSKSHT (SEQ ID No. 3) to Gd-DOTA makes it possible to specifically target the Con-A-induced hepatitis in the mouse, via the targeting of VCAM-1.

II.3.2.2. MRI In Vivo on ApoE$^{-/-}$ Mice

Dynamic monitoring of the MRI signal on a model of atherosclerosis (apoE$^{-/-}$ mouse) shows that the grafting of the peptide NNSKSHT (SEQ ID No. 3) to Gd-DOTA makes it possible to specifically target the atheroma plaque, via a probable targeting of VCAM-1. In fact, i.v. injection of the Gd-DOTA-NNSKSHT, at the dose of 100 μmol Gd/kg, makes it possible to detect a signal enhancement greater than that measured with the ungrafted Gd-DOTA product, at the level of the abdominal aorta. This difference is observed with the two MRI sequences (RARE and MSME) for all the acquisition times (7-60 min post-injection of contrast product).

Figure 4:
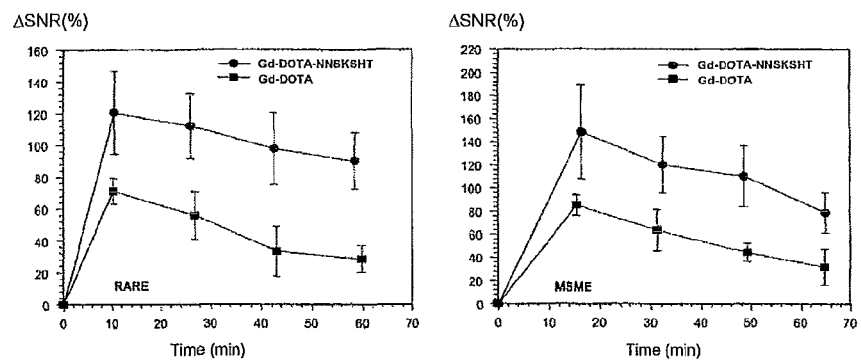

FIG. 4: dynamic monitoring of the targeting of the atheroma plaque in apoE$^{-/-}$ mice (n=4-6) after injection of Gd-DOTA or Gd-DOTA-NNSKSHT (100 μmol Gd/kg i.v.). RARE and MSME sequences.

Figure 5:
Figure 5:
Figure 5:
Figure 5:
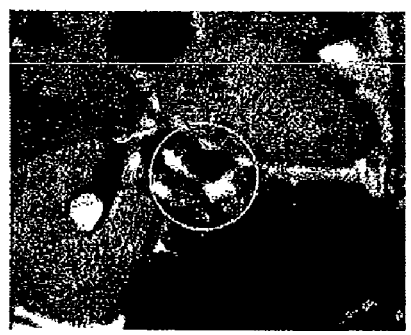
Figure 5:
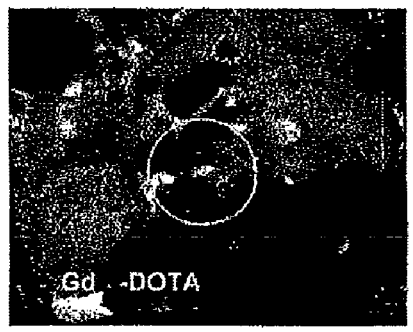
Figure 5:
Figure 5:
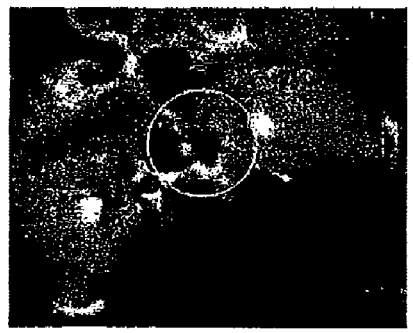
Figure 5:
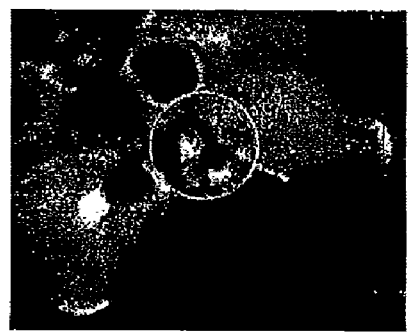

FIG. 5: targeting of the atheroma plaque in an apoE$^{-/-}$ mouse after injection of Gd-DOTA or of Gd-DOTA-NNSKSHT (100 μmol Gd/kg i.v.). MRI of serial slices of the abdominal aorta (circled region) over a length of 3.2 mm. RARE sequence, 27 minutes after injection of contrast product. The enhancement (white) of the circled region corresponds to the atheroma plaque.

The invention claimed is:

1. A compound of general formula (I) below:

Signal-Linker-Peptide       (I)

in which:
Signal is a signal entity;
Linker, which is absent or is a chemical bond, and
Peptide is a peptide comprising a VCAM-targeting peptide, the VCAM-targeting peptide defined below:
X10-X11-X12-X13-X14-X15-X16-X17-X18 (SEQ ID No. 4) with:

X10 selected from cysteine and methionine
X11 selected from methionine and cysteine
X12 selected from lysine, arginine and alanine
X13 selected from threonine and serine
X14 selected from aspartic acid and glutamic acid
X15 selected from threonine and serine
X16 selected from arginine, alanine and lysine
X17 selected from leucine, isoleucine and valine
X18 selected from cysteine and methionine and the pharmaceutically acceptable salts of a),
wherein the signal entity is selected from the group consisting of: (1) a chelate coupled to a paramagnetic metal;

(2) a metal nanoparticle; and (3) a lipid nanoparticle coupled to a paramagnetic chelate, and (4) a chelate coupled to a radionuclide selected from the radioactive forms of elements consisting of: Sm, Ho, Y, Pm, Gd, La, Lu, Yb, Sc, Pr, Tc, Re, Ru, Rh, Pd, Pt, Cu, Au, Ga, In, Sn, Cr, and P.

2. The compound as claimed in claim 1, in which the radionuclide is Ga68 for PET imaging.

3. The compound as claimed in claim 1, in which the chelate is selected from: DOTA, DTPA, DO3A, HPDO3A, TRITA, TETA, BOPTA, NOTA, PCTA, DOTMA, AAZTA, HOPO and their derivatives,
wherein the derivatives are selected from the group consisting of: DTPA-BMA, LICAM and MECAM.

4. The compound as claimed in claim 1, in which Linker is:
a) a group of formula: Q1-1-Q2,
in which Q1 and Q2, is independently selected from O, S, NH, CO$_2$, —NHCO, CONH, NHCONH, NHC-SNH, SO$_2$NH— or NHSO$_2$—,
and 1 is an alkyl group, alkoxyalkyl group polyalkoxyalkylene group, alkenyl group, alkynyl group, alkyl group interrupted with one or more squarates, with one or more aryls, or with one or more groups selected from —NH—, —O—, —CO—, —NH(CO)—, —(CO)NH—, —O(CO)— or —(OC)O—;
b) a (CH$_2$)$_n$, (CH$_2$)$_n$—CO—, —(CH$_2$)$_n$NH—CO—, where n=2 to 10, (CH$_2$CH$_2$O)$_q$(CH$_2$)$_r$—CO—, (CH$_2$CH$_2$O)$_q$(CH$_2$)$_r$—NH—CO—, where q=1-10 and r=2-10, (CH$_2$)$_n$—CONH—, (CH$_2$)$_n$—CONH-PEG, (CH$_2$)$_n$—NH—,

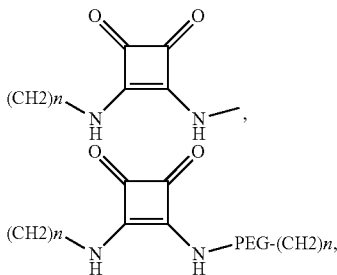

where n=1 to 5, HOOC—CH$_2$—O—(CH$_2$)$_2$—O—(CH$_2$)$_2$—O—CH$_2$—COOH; HOOC—(CH$_2$)$_2$—CO$_2$—(CH$_2$)$_2$—OCO—(CH$_2$)$_2$—COOH; HOOC—CH(OH)—CH(OH)—COOH; HOOC—(CH$_2$)$_n$—COOH; NH$_2$—(CH$_2$)$_n$—NH$_2$, where n=1-20; NH$_2$—(CH$_2$)$_n$—CO$_2$H; or NH$_2$—CH$_2$—(CH$_2$—O—CH$_2$)$_n$—CO$_2$H, where n=1 to 10, group.

5. The compound as claimed in claim 1, in which Signal is a lipid nanoparticle comprising at least one chelate.

6. A composition for medical imaging, comprising at least one compound of general formula (I) as claimed in claim 1 and a pharmaceutically acceptable excipient.

7. A method for the diagnosis of cardiovascular diseases and/or of a risk of ischemic attack comprising the administration of general formula (I) as claimed in claim 1, to a patient in need thereof,
wherein the cardiovascular disease is selected from the group consisting of:
atherosclerosis, an atheroma plaque, angina, thrombosis, cerebral stroke, myocardial infarction, vascular stenosis, infarction, and
wherein the risk of ischemic attack is selected from the group consisting of: myocardial infarction, a cerebral stroke, a renal embolism, acute limb ischemia and a ruptured aortic aneurysm.

8. The method as claimed in claim 7, in which the cardiovascular disease is coronary artery disease.

9. The method as claimed in claim 7, in which the risk of ischemic attack is selected from: myocardial infarction, a cerebral stroke, a renal embolism, acute limb ischemia and a ruptured aortic aneurysm.

10. The compound as claimed in claim 1 in which the peptide is CMKTDTRLC (SEQ ID No. 5).

11. The compound as claimed in claim 5 in which the chelate is as defined in claim 3.

12. The composition as claimed in claim 6 in which the excipient is for parenteral administration.

13. The compound as claimed in claim 1, in which the radionuclide is selected from the group consisting of $^{99}$TC, $^{117}$Sn, $^{111}$In, $^{97}$Ru, $^{67}$Ga, $^{68}$Ga, $^{89}$Zr, $^{177}$Lu, $^{47}$SC, $^{105}$Rh, $^{188}$R, $^{60}$Cu, $^{62}$Cu, $^{64}$Cu, $^{67}$Cu, $^{90}$Y, $^{159}$Gd, $^{149}$Pr, $^{166}$Ho and $^{68}$Ga.

* * * * *

UNITED STATES PATENT AND TRADEMARK OFFICE
CERTIFICATE OF CORRECTION

PATENT NO. : 8,367,039 B2  
APPLICATION NO. : 12/593175  
DATED : February 5, 2013  
INVENTOR(S) : Marc Port et al.

Page 1 of 1

It is certified that error appears in the above-identified patent and that said Letters Patent is hereby corrected as shown below:

IN THE SPECIFICATION:

At column 6, replace the two formulae at lines 1-10, with the following corrected formulae:

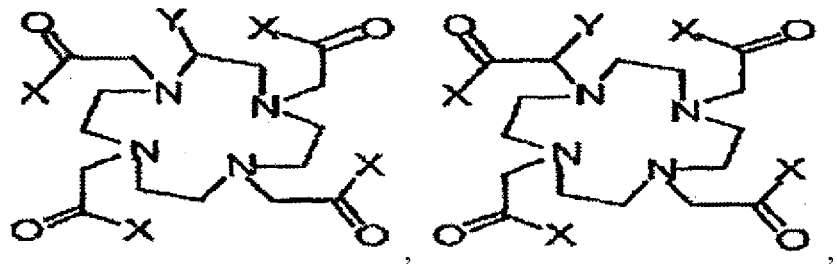

Signed and Sealed this  
Seventeenth Day of December, 2013

Margaret A. Focarino  
*Commissioner for Patents of the United States Patent and Trademark Office*

SEQUENCE LISTING

<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide: VCAM marker
<220> FEATURE:
<221> NAME/KEY: VARIANT
<222> LOCATION: (1)..(1)
<223> OTHER INFORMATION: Xaa, if present, is cysteine or methionine
<220> FEATURE:
<221> NAME/KEY: VARIANT
<222> LOCATION: (2)..(3)
<223> OTHER INFORMATION: Xaa is asparagine or glutamine
<220> FEATURE:

```
<221> NAME/KEY: VARIANT
<222> LOCATION: (4)..(4)
<223> OTHER INFORMATION: Xaa is serine or threonine
<220> FEATURE:
<221> NAME/KEY: VARIANT
<222> LOCATION: (5)..(5)
<223> OTHER INFORMATION: Xaa is lysine, arginine, histidine or ornithine
<220> FEATURE:
<221> NAME/KEY: VARIANT
<222> LOCATION: (6)..(6)
<223> OTHER INFORMATION: Xaa is serine or threonine
<220> FEATURE:
<221> NAME/KEY: VARIANT
<222> LOCATION: (7)..(7)
<223> OTHER INFORMATION: Xaa is histidine, arginine or lysine
<220> FEATURE:
<221> NAME/KEY: VARIANT
<222> LOCATION: (8)..(8)
<223> OTHER INFORMATION: Xaa is threonine or serine
<220> FEATURE:
<221> NAME/KEY: VARIANT
<222> LOCATION: (9)..(9)
<223> OTHER INFORMATION: Xaa, if present, is cysteine or methionine

<400> SEQUENCE: 1

Xaa Xaa Xaa Xaa Xaa Xaa Xaa Xaa Xaa
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide: VCAM marker

<400> SEQUENCE: 2

Cys Asn Asn Ser Lys Ser His Thr Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide: VCAM marker

<400> SEQUENCE: 3

Asn Asn Ser Lys Ser His Thr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide: VCAM marker
<220> FEATURE:
<221> NAME/KEY: VARIANT
<222> LOCATION: (1)..(2)
<223> OTHER INFORMATION: Xaa is cysteine or methionine
<220> FEATURE:
<221> NAME/KEY: VARIANT
<222> LOCATION: (3)..(3)
<223> OTHER INFORMATION: Xaa is lysine, arginine or alanine
<220> FEATURE:
<221> NAME/KEY: VARIANT
<222> LOCATION: (4)..(4)
<223> OTHER INFORMATION: Xaa is threonine or serine
<220> FEATURE:
<221> NAME/KEY: VARIANT
<222> LOCATION: (5)..(5)
<223> OTHER INFORMATION: Xaa is aspartic acid or glutamic acid
<220> FEATURE:
<221> NAME/KEY: VARIANT
```

```
<222> LOCATION: (6)..(6)
<223> OTHER INFORMATION: Xaa is threonine or serine
<220> FEATURE:
<221> NAME/KEY: VARIANT
<222> LOCATION: (7)..(7)
<223> OTHER INFORMATION: Xaa is arginine, alanine or lysine
<220> FEATURE:
<221> NAME/KEY: VARIANT
<222> LOCATION: (8)..(8)
<223> OTHER INFORMATION: Xaa is leucine, isoleucine or valine
<220> FEATURE:
<221> NAME/KEY: VARIANT
<222> LOCATION: (9)..(9)
<223> OTHER INFORMATION: Xaa is cysteine or methionine

<400> SEQUENCE: 4

Xaa Xaa Xaa Xaa Xaa Xaa Xaa Xaa Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide: VCAM marker

<400> SEQUENCE: 5

Cys Met Lys Thr Asp Thr Arg Leu Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

His Ser Cys Asn Lys Asn Ser Cys Thr
1               5

<210> SEQ ID NO 7
<211> LENGTH: 40
<212> TYPE: PRT
<213> ORGANISM: Artificial Sequence
<220> FEATURE:
<223> OTHER INFORMATION: Synthetic peptide

<400> SEQUENCE: 7

Met Leu Pro Phe Ser Phe Thr Gln Tyr Gln Gly Gly Asn Gly Ser Ser
1               5                   10                  15

Pro Val Arg Gly Ile Pro Pro Ala Ile Arg Ser Pro Gln Asn Ser His
                20                  25                  30

Ser His Ser Thr Pro Ser Ser Ser
            35                  40
```